(12) United States Patent
Galili

(10) Patent No.: US 9,662,383 B2
(45) Date of Patent: May 30, 2017

(54) COMPOSITIONS AND METHODS FOR INCREASING IMMUNOGENICITY OF GLYCOPROTEIN VACCINES

(75) Inventor: Uri Galili, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 866 days.

(21) Appl. No.: 12/450,384

(22) PCT Filed: Mar. 26, 2008

(86) PCT No.: PCT/US2008/004020
§ 371 (c)(1),
(2), (4) Date: Jan. 20, 2010

(87) PCT Pub. No.: WO2008/118487
PCT Pub. Date: Oct. 2, 2008

(65) Prior Publication Data
US 2010/0145015 A1    Jun. 10, 2010

Related U.S. Application Data

(60) Provisional application No. 60/920,221, filed on Mar. 26, 2007.

(51) Int. Cl.
| | | |
|---|---|---|
| *A61K 39/395* | (2006.01) | |
| *C07K 14/00* | (2006.01) | |
| *C07K 16/18* | (2006.01) | |
| *C12N 15/11* | (2006.01) | |
| *G01N 33/53* | (2006.01) | |
| *A61K 39/145* | (2006.01) | |
| *C07K 14/005* | (2006.01) | |
| *C12N 7/00* | (2006.01) | |
| *C12N 9/10* | (2006.01) | |
| *A61K 39/385* | (2006.01) | |
| *A61K 39/12* | (2006.01) | |
| *A61K 39/00* | (2006.01) | |

(52) U.S. Cl.
CPC ............ *A61K 39/145* (2013.01); *A61K 39/12* (2013.01); *A61K 39/385* (2013.01); *C07K 14/005* (2013.01); *C12N 7/00* (2013.01); *C12N 9/1051* (2013.01); *C12N 9/1081* (2013.01); *C12Y 204/01087* (2013.01); *C12Y 302/01018* (2013.01); *A61K 2039/5252* (2013.01); *A61K 2039/55566* (2013.01); *A61K 2039/6031* (2013.01); *A61K 2039/6087* (2013.01); *C07K 2319/91* (2013.01); *C12N 2760/16122* (2013.01); *C12N 2760/16134* (2013.01); *C12N 2760/16152* (2013.01); *C12N 2760/16222* (2013.01); *C12N 2760/16252* (2013.01)

(58) Field of Classification Search
CPC ........ C07K 14/005; C12N 2760/16122; C12N 15/86; C12N 2710/10343

USPC ....................................................... 435/6; 3/6
See application file for complete search history.

(56) References Cited

U.S. PATENT DOCUMENTS

| 5,879,675 A | 3/1999 | Galili ........................... 424/93.1 |
|---|---|---|
| 6,361,775 B1 * | 3/2002 | Galili ..................... A61K 39/00 424/155.1 |

FOREIGN PATENT DOCUMENTS

| WO | WO9949029 | * | 9/1999 |
|---|---|---|---|
| WO | WO02068632 | * | 9/2002 |
| WO | WO03088995 | * | 10/2003 |
| WO | WO2005062820 | * | 7/2005 |

OTHER PUBLICATIONS

Larsen, et al. Isolation of a cDNA encoding a murine UDPgalactose:β-D-galactosyl-1,4-N-acetyl-D-glucosaminide α-l,3-galactosyltransferase: Expression cloning by gene transfer. Proc. Natl. Acad. Sci. USA. 1989; 86: 8227-8231.*
Long, et al. Establishment of reverse genetics system for H5N1 subtype AI. Weishengwu Xuebao. 2006; 46(1): 55-59. Abstract Only.*
Wissman, MA. Caring for Marmosets & Tamarins. 2006; downloaded from http://www.exoticpetvet.net/primate/care.html on Sep. 27, 2012.*
Henion et al., "Synthesis of a-gal epitopes on influenza virus vaccines, by recombinant a1,3galactosyltransferase, enables the formation of immune complexes with the natural anti-Gal antibody", 1997, Vaccine, 15(11):1174-1182.*
Deriy et al., "Expression of alpha-gal epitopes on HeLa cells transduced with adenovirus containing a1,3 galactosyltransferase cDNA", Glycobiology, 2002, 12(2):135-144.*
Altschul, S. F. and Gish, W. (1996) [27] Local alignment statistics, in *Methods in Enzymology* (Russell, F. D., Ed.), pp. 460-480, Academic Press.
CDC Fact Sheet 2006.
Abdel-Motal, U. et al. (2006) Increased Immunogenicity of Human Immunodeficiency Virus gp120 Engineered to Express Galα1-3Galβ1-4GlcNAc-R Epitopes, *Journal of Virology* 80(14), 6943-6951.

(Continued)

*Primary Examiner* — Janet L Andres
*Assistant Examiner* — Barry A Chestnut
(74) *Attorney, Agent, or Firm* — Medlen & Carroll, LLP

(57) ABSTRACT

The present invention relates to the microbial immunogens engineered to bear α-gal epitope(s) for induction of potent humoral and cellular immune responses when administered to subjects having anti-Gal antibodies. In one embodiment, the present invention provides compositions and methods for propagating influenza virus in human, ape, Old World monkey or bird cells that have been engineered to express an α1,3galactosyltransferase (α 1,3GT) gene to produce virions bearing hemagglutinin molecules containing α-gal epitopes, to increase the immunogenicity of the influenza virus. In another embodiment, the present invention provides fusion proteins between influenza virus hemagglutinin and a microbial peptide or protein of interest, and enzymatic processing of this fusion protein to carry α-gal epitopes, to increase the immunogenicity of the microbial peptide or protein of interest.

13 Claims, 13 Drawing Sheets

(56) References Cited

OTHER PUBLICATIONS

Altschul, S. F. et al. (1990) Basic local alignment search tool, *Journal of Molecular Biology* 215(3), 403-410.
Black, R. A. et al. (1993) Antibody response to the M2 protein of influenza A virus expressed in insect cells, *Journal of General Virology* 74(1), 143-146.
Chen, Z. C. et al. (2001) Synthesis of α-gal epitopes (Galα1-3Galβ1-4GlcNAc-R) on human tumor cells by recombinant α1,3galactosyltransferase produced in Pichia pastoris, *Glycobiology* 11(7), 577-586.
Clynes, R. et al. (1998) Fc receptors are required in passive and active immunity to melanoma, *Proceedings of the National Academy of Sciences* 95(2), 652-656.
Collins, B. H. et al. (1995) Cardiac xenografts between primate species provide evidence for the importance of the alpha-galactosyl determinant in hyperacute rejection, *The Journal of Immunology* 154(10), 5500-5510.
Cotter, P. and Van Eerden, E. (2006) Natural anti-Gal and *Salmonella*-specific antibodies in bile and plasma of hens differing in diet efficiency, *Poultry Science* 85(3), 435-440.
de Jong, M. D. et al. (2006) Fatal outcome of human influenza A (H5N1) is associated with high viral load and hypercytokinemia, *Nat Med* 12(10), 1203-1207.
Devereux, J. et al. (1984) A comprehensive set of sequence analysis programs for the VAX, *Nucleic Acids Research* 12(1Part1), 387-395.
Diamond, L. et al. (2002) Analysis of the control of the anti-gal immune response in a non-human primate by galactose alpha1-3 galactose trisaccharide-polyethylene glycol conjugate, *Transplantation* 73(11), 1780-1787.
Flynn, K. J. et al. (1999) In vivo proliferation of naïve and memory influenza-specific CD8+ T cells, *Proceedings of the National Academy of Sciences* 96(15), 8597-8602.
Galili, U. (1993) Interaction of the natural anti-Gal antibody with α-galactosyl epitopes: a major obstacle for xenotransplantation in humans, *Immunology Today* 14(10), 480-482.
Galili, U. (1993) Evolution and pathophysiology of the human natural anti-α-galactosyl IgG (anti-Gal) antibody, *Springer Seminars in Immunopathology* 15(2), 155-171.
Galili, U. (2005) The α-gal epitope and the anti-Gal antibody in xenotransplantation and in cancer immunotherapy, *Immunology & Cell Biology* 83(6), 674-686.
Galili, U. et al. (1998) A Sensitive Assay for Measuring-Gal Epitope Expression on Cells by a Monoclonal Anti-Gal Antibody, *Transplantation* 65(8), 1129-1132.
Galili, U. et al. (1988) Interaction between human natural anti-alpha-galactosyl immunoglobulin G and bacteria of the human flora, *Infection and Immunity* 56(7), 1730-1737.
Galili, U. et al. (1984) A unique natural human IgG antibody with anti-alpha-galactosyl specificity, *Journal of Experimental Medicine* 160(5), 1519-1531.
Galili, U. et al. (1996) Enhancement of antigen presentation of influenza virus hemagglutinin by the natural human anti-Gal antibody, *Vaccine* 14(4), 321-328.
Galili, U. et al. (1988) Man, apes, and Old World monkeys differ from other mammals in the expression of alpha-galactosyl epitopes on nucleated cells, *Journal of Biological Chemistry* 263(33), 17755-17762.
Govorkova, E. A. et al. (1996) African green monkey kidney (Vero) cells provide an alternative host cell system for influenza A and B viruses, *Journal of Virology* 70(8), 5519-5524.
Henion, T. R. et al. (1997) Synthesis of α-gal epitopes on influenza virus vaccines, by recombinant α1,3galactosyltransferase, enables the formation of immune complexes with the natural anti-Gal antibody, *Vaccine* 15(11), 1174-1182.
Houston, W. E. et al. (1977) Inactivated Venezuelan Equine Encephalomyelitis Virus Vaccine Complexed with Specific Antibody: Enhanced Primary Immune Response and Altered Pattern of Antibody Class Elicited, *The Journal of Infectious Diseases* 135(4), 600-610.
Karlin, S. and Altschul, S. F. (1993) Applications and statistics for multiple high-scoring segments in molecular sequences, *Proceedings of the National Academy of Sciences* 90(12), 5873-5877.
Macken, C. et al. (2001) The value of a database in surveillance and vaccine selection, *International Congress Series* 1219(0), 103-106.
Manca, F. et al. (1991) Effect of antigen/antibody ratio on macrophage uptake, processing, and presentation to T cells of antigen complexed with polyclonal antibodies, *The Journal of Experimental Medicine* 173(1), 37-48.
McKenzie, I. F. C. et al. (1999) Definition and Characterization of Chicken Gal (1, 3) Gal Antibodies, *Transplantation* 67(6), 864-870.
Mozdzanowska, K. et al. (2003) Induction of influenza type A virus-specific resistance by immunization of mice with a synthetic multiple antigenic peptide vaccine that contains ectodomains of matrix protein 2, *Vaccine* 21(19-20), 2616-2626.
Pearson, W. R. and Lipman, D. J. (1988) Improved tools for biological sequence comparison, *Proceedings of the National Academy of Sciences* 85(8), 2444-2448.
Potvin, B. et al. (1995) lec32 Is a New Mutation in Chinese Hamster Ovary Cells That Essentially Abrogates CMP-N-acetylneuraminic Acid Synthetase Activity, *Journal of Biological Chemistry* 270(51), 30415-30421.
Regnault, A. et al. (1999) Fcγ Receptor—mediated Induction of Dendritic Cell Maturation and Major Histocompatibility Complex Class I—restricted Antigen Presentation after Immune Complex Internalization, *The Journal of Experimental Medicine* 189(2), 371-380.
Repik, P. M. et al. (1994) Differential Host-dependent Expression of α-galactosyl Epitopes on Viral Glycoproteins: A Study of Eastern Equine Encephalitis Virus as a Model, *Journal of General Virology* 75(5), 1177-1181.
Riberdy, J. M. et al. (1999) Protection against a Lethal Avian Influenza A Virus in a Mammalian System, *Journal of Virology* 73(2), 1453-1459.
Smith, D. F. et al. (1990) Transfer and expression of a murine UDP-Gal:beta-D-Gal-alpha 1,3-galactosyltransferase gene in transfected Chinese hamster ovary cells. Competition reactions between the alpha 1,3-galactosyltransferase and the endogenous alpha 2,3-sialyltransferase, *Journal of Biological Chemistry* 265(11), 6225-6234.
Tanemura, M. et al. (2002) Elimination of anti-Gal B cells by -Gal ricin, *Transplantation* 73(12), 1859-1868.
Thall, A. D. et al. (1995) Oocyte Galα1,3Gal Epitopes Implicated in Sperm Adhesion to the Zona Pellucida Glycoprotein ZP3 Are Not Required for Fertilization in the Mouse, *Journal of Biological Chemistry* 270(37), 21437-21440.
Unkeless, J. C. (1989) Function and heterogeneity of human Fc receptors for immunoglobulin G, *Journal of Clinical Investigation* 83(2), 355-361.
Villinger, F. et al. (2003) Evidence for Antibody-Mediated Enhancement of Simian Immunodeficiency Virus (SIV) Gag Antigen Processing and Cross Presentation in SIV-Infected Rhesus Macaques, *Journal of Virology* 77(1), 10-24.
Webster, R. G. (2000) Immunity to influenza in the elderly, *Vaccine* 18(16), 1686-1689.
Zhang, M. et al. (2006) Fine specificity and sequence of antibodies directed against the ectodomain of matrix protein 2 of influenza A virus, *Molecular Immunology* 43(14), 2195-2206.
Zhong, R. et al. (2003) Improvement in human decay accelerating factor transgenic porcine kidney xenograft rejection with intravenous administration of gas914, a polymeric form of gal, *Transplantation* 75(1), 10-19.
Zinkernagel, R. M. et al. (1997) Antigen localisation regulates immune responses in a dose- and time-dependent fashion: a geographical view of immune reactivity, *Immunological Reviews* 156(1), 199-209.
LaTemple, D.C., J.T. Abrams, S.U. Zhang and U. Galili. Increased immunogenicity of tumor vaccines complexed with anti-Gal: Studies in knock out mice for a1,3galactosyltranferase. Cancer Research, 59: 3417-3423, 1999.
Galili, U., S.B. Shohet, E. Kobrin, C.L.M. Stults and B.A. Macher. Man, apes, and Old World monkeys differ from other mammals in the expression of α-galactosyl epitopes on nucleated cells. J. Biol.

(56) References Cited

OTHER PUBLICATIONS

Chem. 263:17755-17762, 1988; Henion, T.R., B.A. Macher, F. Anaraki and U. Galili. Defining the minimal size of catalytically active primate α1,3 galactosyltransferase: Structure function studies on the recombinant truncated enzyme. Glycobiology 4:193-201, 1994.

Macher, B. A, and U. Galili. The Galα1,3Galα1,4GlcNAc-R (α-Gal) epitope: a carbohydrate of unique evolution and clinical relevance. Biochem. Biophys. Acta. 1780: 75-88, 2008.

Henion, T.R., B.A. Macher, F. Anaraki and U. Galili. Defining the minimal size of catalytically active primate α1,3 galactosyltransferase: Structure function studies on the recombinant truncated enzyme. Glycobiology 4:193-201, 1994.

Deriy, L., Z. Chen, G. Gao and U. Galili. Expression of a-Gal epitopes (Gal a1-3Gal b1-4GlcNAc-R) on human cells following transduction with adenovirus vector containing a1,3galactosyltransferase cDNA. Glycobiology, 12:135-144, 2002.

* cited by examiner

A. Anti-PR8 IgG in KO mice

B. Anti-PR8 IgG in WT mice

C. Anti-PR8 IgA in KO mice

Production of HA-M2e Fusion Protein

Production of HA-NP Fusion Protein

1) Restriction site+5' HA → HA GlyGlyGly
   ← 3' of HA+ GlyGlyGly

5' NP (+GlyGlyGly+3'HA) ⋯> NP
   <⋯ 3' of NP(+His6+restriction site)

2) Restriction site, 5' HA → HA GlyGlyGly →
   ← NP <⋯
   3' of NP(+His6+restriction site)

3) Restriction site ———— GlyGlyGly ⋯⋯His(6) restriction site
   HA-NP

FIG. 9

FIG. 10A common marmoset GGTA1 nucleic acid sequence (SEQ ID NO:1)

```
   1 atgaatgtca aaggaaaagt aattctgtcg atgctggttg tctcaactgt gattgttgtg
  61 ttttgggaat atatcaacag cccagaaggc tctttcttgt ggatatatca ctcaaagaac
 121 ccagaagttg atgacagcag tgctcagaag gactggtggt ttcctggctg gtttaacaat
 181 gggatccaca attatcaaca agaggaagaa gacacagaca aagaaaaagg aagagaggag
 241 gaacaaaaaa aggaagatga cacaacagag cttcggctat gggactggtt taatccaaag
 301 aaacgcccag aggttatgac agtgacccaa tggaaggcgc cggttgtgtg ggaaggcact
 361 tacaacaaag ccatcctaga aaattattat gccaaacaga aaattaccgt ggggttgacg
 421 gtttttgcta ttggaagata tattgagcat tacttggagg agttcgtaac atctgctaat
 481 aggtacttca tggtcggcca caaagtcata ttttatgtca tggtggatga tgtctccaag
 541 gcgccgttta tagagctggg tcctctgcgt tccttcaaag tgtttgaggt caagccagag
 601 aagaggtggc aagacatcag catgatgcgt atgaagacca tcggggagca catcttggcc
 661 cacatccaac acgaggttga cttcctcttc tgcatggatg tggaccaggt cttccaagac
 721 catttttgggg tagagaccct gggccagtcg gtggctcagc tacaggcctg gtggtacaag
 781 gcagatcctg atgactttac ctatgagagg cggaaagagt cggcagcata tattccattt
 841 ggccaggggg attttatta ccatgcagcc atttttggag gaacaccgat tcaggttctc
 901 aacatcaccc aggagtgctt taagggaatc ctcctggaca agaaaaatga catagaagcc
 961 gagtggcatg atgaaagcca cctaaacaag tatttccttc tcaacaaacc ctctaaaatc
1021 ttatctccag aatactgctg ggattatcat ataggcctgc cttcagatat taaaactgtc
1081 aagctatcat ggcaaacaaa agagtataat ttggttagaa agaatgtctg a
```

FIG. 10B common marmoset GGTA1 amino acid sequence (SEQ ID NO:2)

```
  1 MNVKGKVILS MLVVSTVIVV FWEYINSPEG SFLWIYHSKN PEVDDSSAQK DWWFPGWFNN
 61 GIHNYQQEEE DTDKEKGREE EQKKEDDTTE LRLWDWFNPK KRPEVMTVTQ WKAPVVWEGT
121 YNKAILENYY AKQKITVGLT VFAIGRYIEH YLEEFVTSAN RYFMVGHKVI FYVMVDDVSK
181 APFIELGPLR SFKVFEVKPE KRWQDISMMR MKTIGEHILA HIQHEVDFLF CMDVDQVFQD
241 HFGVETLGQS VAQLQAWWYK ADPDDFTYER RKESAAYIPF GQGDFYYHAA IFGGTPIQVL
301 NITQECFKGI LLDKKNDIEA EWHDESHLNK YFLLNKPSKI LSPEYCWDYH IGLPSDIKTV
361 KLSWQTKEYN LVRKNV
```

FIG. 11A mouse GGTA1 nucleic acid sequence (SEQ ID NO:3)

```
   1 atgaatgtca agggaaaagt aatcctgttg atgctgattg tctcaaccgt ggttgtcgtg
  61 ttttgggaat atgtcaacag cccagacggc tctttcttgt ggatatatca cacaaaaatt
 121 ccagaggttg gtgagaacag atggcagaag gactggtggt tcccaagctg gtttaaaaat
 181 gggacccaca gttatcaaga agacaacgta gaaggacgga gagaaaaggg tagaaatgga
 241 gatcgcattg aagagcctca gctatgggac tggttcaatc caaagaaccg cccggatgtt
 301 ttgacagtga ccccgtggaa ggcgccgatt gtgtgggaag gcacttatga cacagctctg
 361 ctggaaaagt actacgccac acagaaactc actgtgggcc tgacagtgtt tgctgtggga
 421 aagtacattg agcattactt agaagactttc ctggagtctg ctgacatgta cttcatggtt
 481 ggccatcggg tcatatttta cgtcatgata gatgacacct cccggatgcc tgtcgtgcac
 541 ctgaaccctc tacattcctt acaagtcttt gagatcaggt ctgagaagag gtggcaggat
 601 atcagcatga tgcgcatgaa gaccattggg gagcacatcc tggcccacat ccagcacgag
 661 gtcgacttcc tcttctgcat ggacgtggat caagtctttc aagacaactt cggggtggaa
 721 actctgggcc agctggtagc acagctccag gcctggtggt acaaggccag tcccgagaag
 781 ttcacctatg agaggcggga actgtcggcc gcgtacattc cattcggaga ggggattttt
 841 tactaccacg cggccatttt tggaggaacg cctactcaca ttctcaacct caccagggag
 901 tgctttaagg ggatcctcca ggacaagaaa catgacatag aagcccagtg gcatgatgag
 961 agccacctca acaaatactt ccttttcaac aaacccacta aatcctatc tccagagtat
1021 tgctgggact atcagatagg cctgccttca gatattaaaa gtgtcaaggt agcttggcag
1081 acaaaagagt ataatttggt tagaaataat gtctga
```

FIG. 11B mouse GGTA1 amino acid sequence (SEQ ID NO:4)

```
  1 MNVKGKVILL MLIVSTVVVV FWEYVNSPDG SFLWIYHTKI PEVGENRWQK DWWFPSWFKN
 61 GTHSYQEDNV EGRREKGRNG DRIEEPQLWD WFNPKNRPDV LTVTPWKAPI VWEGTYDTAL
121 LEKYYATQKL TVGLTVFAVG KYIEHYLEDF LESADMYFMV GHRVIFYVMI DDTSRMPVVH
181 LNPLHSLQVF EIRSEKRWQD ISMMRMKTIG EHILAHIQHE VDFLFCMDVD QVFQDNFGVE
241 TLGQLVAQLQ AWWYKASPEK FTYERRELSA AYIPFGEGDF YYHAAIFGGT PTHILNLTRE
301 CFKGILQDKK HDIEAQWHDE SHLNKYFLFN KPTKILSPEY CWDYQIGLPS DIKSVKVAWQ
361 TKEYNLVRNN V
```

FIG. 12

CLUSTAL W (1.82) multiple sequence alignment

```
marmoset    MNVKGKVILSMLVVSTVIVVFWEYINSPEGSFLWIYHSKNPEVDD-SSAQKDWWFPGWFN
mouse       MNVKGKVILLMLIVSTVVVVFWEYVNRTHSYQEDNVEGRR--------------------
cow         MNVKGKVILSMLVVSTVIVVFWEYIHSPEGSLFWINPSRNPEVGG-SSIQKGWWLPRWFN
cat         MNVKGRVVLSMLVVSTVIVVFWEYINSPEGSFLWIYHSKNPEVGD-SSTQKGWWFPSWFN
sheep       MNVKGKVILSMLVVSTVIVVFWEYIHSPEGSLFWINPSRNPEVSGGSSIQKGWWFPRWFN
rat         MNVKGKIILSVLMVSTVLVVFWEYVNRTHSYQEEDIERAR--------------------
pig         MNVKGRVVLSMLLVSTVMVVFWEYINSPEGSLFWIYQSKNPEVG--SSAQRGWWFPSWFN
            *****::.:* :*:****:******::  ...

marmoset    NGIHNYQQEEEDTDKEKGREEEQKKEDDTTELRLWDWFNPKKRPEVMTVTQWKAPVVWEG
mouse       -------------------EKGRNGDRIEEPQLWDWFNPKNRPDVLTVTPWKAPIVWEG
cow         NGYH----EEDGD----INEEKEQRNEDESKLKLSDWFNPFKRPEVVTMTKWKAPVVWEG
cat         NRTHSYPEEE--A----VDEGDEQRKENSEELQLSDWFNPQKRPDVVTVTEWKAPVVWEG
sheep       NGYQ----EEDED----VDEEKEQRKEDKSKLKLSDWFNPFKRPEVVTMTDWKAPVVWEG
rat         -------------------EKGRNGDSIVEPQLWDWFNPKNRPEVLTVTPWKAPIVWEG
pig         NGTHSYHEEEDAI----GNEKEQRKEDNRGELPLVDWFNPEKRPEVVTITRWKAPVVWEG
                        . :. :   :  * ***** :**:*:*:* ****:****

marmoset    TYNKAILENYYAKQKITVGLTVFAIGRYIEHYLEEFVTSANRYFMVGHKVIFYVMVDDVS
mouse       TYDTALLEKYYATQKLTVGLTVFAVGKYIEHYLEDFLESADMYFMVGHRVIFYVMIDDTS
cow         TYNRAVLDNYYAKQKITVGLTVFAVGRYIEHYLEEFLTSANKHFMVGHPVIFYIMVDDVS
cat         TYNKAILENYYARQKITVGLTVFAVGRYIEHYLEEFLISANRYFMVGHKVIFYIMVDDVS
sheep       TYNRAVLDDYYAKQKITVGLTVFAVGRYIEHYLEEFLTSANKHFMVGHRVIFYVMVDDVS
rat         TYDTALLEKYYARQKITVGLTVFAVGKYIEHYLEDFLESANKYFMVGHRVIFYVMMDDTS
pig         TYNRAVLDNYYAKQKITVGLTVFAVGRYIEHYLEEFLISANTYFMVGHKVIFYIMVDDIS
            **: *:*:.* :**********:*:*******:*: : :* **:*:** * marmoset    KAPFIELGPLRSFKVFEVKPEKRWQDISMMRMKTIGEHILAHIQHEVDFLFCMDVDQVFQ
mouse       RMPVVHLNPLHSLQVFEIRSEKRWQDISMMRMKTIGEHILAHIQHEVDFLFCMDVDQVFQ
cow         RMPLIELGPLRSFKVFKIKPEKRWQDISMMRMKTIGEHIVAHIQHEVDFLFCMDVDQVFQ
cat         KMPLIELGPLRSFKVFEIKPEKRWQDISMMRMKIIGEHIVAHIQHEVDFLFCMDVDQVFQ
sheep       RMPLIELGPLRSFKVFEVKPERRWQDVSMVRMKTIGEHIVAHIQREVDFLFCMDVDQVFQ
rat         RMPAVHLSPLHSLQVFEIRSEKRWQDISMMRMKTIGEHILDHIQHEVDFLFCMDVDQVFQ
pig         RMPLIELGPLRSFKVFEIKSEKRWQDISMMRMKTIGEHILAHIQHEVDFLFCMDVDQVFQ
            : *  :.*.**:*::**::: .*:**::* * :  *:************ marmoset    DHFGVETLGQSVAQLQAWWYKADPDDFTYERRKESAAYIPFGQGDFYYHAAIFGGTPIQV
mouse       DNFGVETLGQLVAQLQAWWYKASPEKFTYERRELSAAYIPFGEGDFYYHAAIFGGTPTHI
cow         DKFGVETLGESVAQLQAWWYKADPNDFTYERRKESAAYIPFGEGDFYYHAAIFGGTPTQV
cat         DSFGVETLGQSVAQLQAWWYKADPDEFTYERRKESAAYIPFGEGDFYYHAAIFGGTPTQV
sheep       DEFGVETLGESVAQLQAWWYKADPDEFTYERRKESAAYIPFGEGDFYYHAAIFGGTPTQV
rat         DNFGVETLGQLVAQLQAWWYKASPDEFTYERRELSAAYIPFGEGDFYYHAAVFGGTPVHI
pig         NNFGVETLGQSVAQLQAWWYKAHPDEFTYERRKESAAYIPFGQGDFYYHAAIFGGTPTQV
            : ******: *********** *:.******: ******:******:*****  ::
```

FIG. 12 continued

```
marmoset    LNITQECFKGILLDKKNDIEAEWHDESHLNKYFLLNKPSKILSPEYCWDYHIGLPSDIKT
mouse       LNLTRECFKGILQDKKHDIEAQWHDESHLNKYFLFNKPTKILSPEYCWDYQIGLPSDIKS
cow         LNITQECFKGILKDKKNDIEAQWHDESHLNKYFLLNKPTKILSPEYCWDYHIGLPADIKL
cat         LNITQECFKGILQDKKNDIEAEWHDESHLNKYFLLNKPTKILSPEYCWDYHIGLPSDIKI
sheep       LNITQECFKGILKDKKNDIEAQWHDESHLNKYFLLNKPTKILSPEYCWDYHIGLPADIKL
rat         LNLTRECFKGILQDKKHDIEAQWHDESHLNKYFLFNKPTKILSPEYCWDYHIGLPSDIKN
pig         LNITQECFKGILQDKENDIEAEWHDESHLNKYFLLNKPTKILSPEYCWDYHIGMSVDIRI
            **:*:*******  **::****:************:***:***********:**:. **:

marmoset    VKLSWQTKEYNLVRKNV
mouse       VKVAWQTKEYNLVRNNV
cow         VKMSWQTKEYNVVRNNV
cat         VKISWQTKEYNLVRNNI
sheep       VKMSWQTKEYNLVRNNV
rat         VKIAWQTKEYNLVRSNV
pig         VKIAWQKKEYNLVRNNI
            **::**.****:**.*:
```

SEQUENCE LISTING

```
<160> NUMBER OF SEQ ID NOS: 13

<210> SEQ ID NO 1
<211> LENGTH: 1131
<212> TYPE: DNA
<213> ORGANISM: Callithrix jacchus

<400> SEQUENCE: 1
atgaatgtca aaggaaaagt aattctgtcg atgctggttg tctcaactgt gattgttgtg      60
```

```
ttttgggaat atatcaacag cccagaaggc tctttcttgt ggatatatca ctcaaagaac   120
ccagaagttg atgacagcag tgctcagaag gactggtggt ttcctggctg gtttaacaat   180
gggatccaca attatcaaca gaggaagaa gacacagaca agaaaaagg aagagaggag    240 gaacaaaaaa aggaagatga cacaacagag cttcggctat gggactggtt taatccaaag   300
aaacgcccag aggttatgac agtgacccaa tggaaggcgc cggttgtgtg ggaaggcact   360
tacaacaaag ccatcctaga aaattattat gccaaacaga aaattaccgt ggggttgacg   420 gttttgcta ttggaagata tattgagcat tacttggagg agttcgtaac atctgctaat    480
aggtacttca tggtcggcca caaagtcata ttttatgtca tggtggatga tgtctccaag   540
gcgccgttta tagagctggg tcctctgcgt tccttcaaag tgtttgaggt caagccagag   600
aagaggtggc aagacatcag catgatgcgt atgaagacca tcgggagca catcttggcc     660 cacatccaac acgaggttga cttcctcttc tgcatggatg tggaccaggt cttccaagac   720
cattttgggg tagagaccct gggccagtcg gtggctcagc tacaggcctg gtggtacaag   780
gcagatcctg atgactttac ctatgagagg cggaaagagt cggcagcata tattccattt   840
ggccaggggg attttttatta ccatgcagcc attttttggag gaacaccgat tcaggttctc   900
aacatcaccc aggagtgctt taagggaatc ctcctgacaa agaaaaatga catagaagcc   960
gagtggcatg atgaaagcca cctaaacaag tatttccttc tcaacaaacc ctctaaaatc   1020
ttatctccag aatactgctg ggattatcat ataggcctgc cttcagatat taaaactgtc   1080
aagctatcat ggcaaacaaa agagtataat ttggttagaa agaatgtctg a            1131
```

<210> SEQ ID NO 2
<211> LENGTH: 376
<212> TYPE: PRT
<213> ORGANISM: Callithrix jacchus

<400> SEQUENCE: 2

```
Met Asn Val Lys Gly Lys Val Ile Leu Ser Met Leu Val Val Ser Thr
1               5                   10                  15

Val Ile Val Val Phe Trp Glu Tyr Ile Asn Ser Pro Glu Gly Ser Phe
            20                  25                  30

Leu Trp Ile Tyr His Ser Lys Asn Pro Glu Val Asp Asp Ser Ser Ala
        35                  40                  45

Gln Lys Asp Trp Trp Phe Pro Gly Trp Phe Asn Asn Gly Ile His Asn
    50                  55                  60

Tyr Gln Gln Glu Glu Glu Asp Thr Asp Lys Lys Lys Gly Arg Glu Glu
65                  70                  75                  80

Glu Gln Lys Lys Glu Asp Asp Thr Thr Glu Leu Arg Leu Trp Asp Trp
                85                  90                  95

Phe Asn Pro Lys Lys Arg Pro Glu Val Met Thr Val Thr Gln Trp Lys
            100                 105                 110

Ala Pro Val Val Trp Glu Gly Thr Tyr Asn Lys Ala Ile Leu Glu Asn
        115                 120                 125

Tyr Tyr Ala Lys Gln Lys Ile Thr Val Gly Leu Thr Val Phe Ala Ile
    130                 135                 140

Gly Arg Tyr Ile Glu His Tyr Leu Glu Glu Phe Val Thr Ser Ala Asn
145                 150                 155                 160

Arg Tyr Phe Met Val Gly His Lys Val Ile Phe Tyr Val Met Val Asp
                165                 170                 175

Asp Val Ser Lys Ala Pro Phe Ile Glu Leu Gly Pro Leu Arg Ser Phe
            180                 185                 190
```

```
Lys Val Phe Glu Val Lys Pro Glu Lys Arg Trp Gln Asp Ile Ser Met
        195                 200                 205
Met Arg Met Lys Thr Ile Gly Glu His Ile Leu Ala His Ile Gln His
    210                 215                 220
Glu Val Asp Phe Leu Phe Cys Met Asp Val Gln Val Phe Gln Asp
225                 230                 235                 240
His Phe Gly Val Glu Thr Leu Gly Gln Ser Val Ala Gln Leu Gln Ala
                245                 250                 255
Trp Trp Tyr Lys Ala Asp Pro Asp Asp Phe Thr Tyr Glu Arg Arg Lys
                260                 265                 270
Glu Ser Ala Ala Tyr Ile Pro Phe Gly Gln Gly Asp Phe Tyr Tyr His
                275                 280                 285
Ala Ala Ile Phe Gly Gly Thr Pro Ile Gln Val Leu Asn Ile Thr Gln
                290                 295                 300
Glu Cys Phe Lys Gly Ile Leu Leu Asp Lys Lys Asn Asp Ile Glu Ala
305                 310                 315                 320
Glu Trp His Asp Glu Ser His Leu Asn Lys Tyr Phe Leu Leu Asn Lys
                325                 330                 335
Pro Ser Lys Ile Leu Ser Pro Glu Tyr Cys Trp Asp Tyr His Ile Gly
                340                 345                 350
Leu Pro Ser Asp Ile Lys Thr Val Lys Leu Ser Trp Gln Thr Lys Glu
                355                 360                 365
Tyr Asn Leu Val Arg Lys Asn Val
                370                 375

<210> SEQ ID NO 3
<211> LENGTH: 1116
<212> TYPE: DNA
<213> ORGANISM: Mus musculus

<400> SEQUENCE: 3
atgaatgtca agggaaaagt aatcctgttg atgctgattg tctcaaccgt ggttgtcgtg      60
ttttgggaat atgtcaacag cccagacggc tctttcttgt ggatatatca cacaaaaatt     120
ccagaggttg gtgagaacag atggcagaag gactggtggt cccaagctg gtttaaaaat      180 gggacccaca gttatcaaga agacaacgta gaaggacgga gagaaaaggg tagaaatgga     240
gatcgcattg aagagcctca gctatgggac tggttcaatc caaagaaccg cccgatgtt     300 ttgacagtga ccccgtggaa ggcgccgatt gtgtgggaag cacttatga cacagctctg     360 ctggaaaagt actacgccac acagaaactc actgtgggc tgacagtgtt tgctgtggga     420
aagtacattg agcattactt agaagacttt ctggagtctg ctgacatgta cttcatggtt     480
ggccatcggg tcatatttta cgtcatgata atgacaccct cccggatgcc tgtcgtgcac     540
ctgaaccctc tacattcctt acaagtcttt gagatcaggt ctgagaagag gtggcaggat     600
atcagcatga tgcgcatgaa gaccattggg gagcacatcc tggcccacat ccagcacgag     660
gtcgacttcc tcttctgcat ggacgtggat caagtctttc aagacaactt cggggtggaa     720
actctgggcc agctggtagc acagctccag gcctggtggt acaaggccag tcccgagaag     780
ttcacctatg agaggcggga actgtcggcc gcgtacattc cattcggaga ggggattttt     840
tactaccacg cggccatttt tggaggaacg cctactcaca ttctcaacct caccagggag     900
tgctttaagg ggatcctcca ggacaagaaa catgacatag aagccagtg gcatgatgag     960 agccacctca caaatactt cctttcaac aaacccacta aatcctatc tccagagtat     1020
```

```
tgctgggact atcagatagg cctgccttca gatattaaaa gtgtcaaggt agcttggcag     1080
acaaaagagt ataatttggt tagaaataat gtctga                              1116
```

<210> SEQ ID NO 4
<211> LENGTH: 371
<212> TYPE: PRT
<213> ORGANISM: Mus musculus

<400> SEQUENCE: 4

```
Met Asn Val Lys Gly Lys Val Ile Leu Leu Met Leu Ile Val Ser Thr
1               5                   10                  15

Val Val Val Val Phe Trp Glu Tyr Val Asn Ser Pro Asp Gly Ser Phe
            20                  25                  30

Leu Trp Ile Tyr His Thr Lys Ile Pro Glu Val Gly Glu Asn Arg Trp
        35                  40                  45

Gln Lys Asp Trp Trp Phe Pro Ser Trp Phe Lys Asn Gly Thr His Ser
    50                  55                  60

Tyr Gln Glu Asp Asn Val Glu Gly Arg Arg Lys Gly Arg Asn Gly
65                  70                  75                  80

Asp Arg Ile Glu Glu Pro Gln Leu Trp Asp Trp Phe Asn Pro Lys Asn
                85                  90                  95

Arg Pro Asp Val Leu Thr Val Thr Pro Trp Lys Ala Pro Ile Val Trp
            100                 105                 110

Glu Gly Thr Tyr Asp Thr Ala Leu Leu Glu Lys Tyr Tyr Ala Thr Gln
        115                 120                 125

Lys Leu Thr Val Gly Leu Thr Val Phe Ala Val Gly Lys Tyr Ile Glu
    130                 135                 140

His Tyr Leu Glu Asp Phe Leu Glu Ser Ala Asp Met Tyr Phe Met Val
145                 150                 155                 160

Gly His Arg Val Ile Phe Tyr Val Met Ile Asp Asp Thr Ser Arg Met
                165                 170                 175

Pro Val Val His Leu Asn Pro Leu His Ser Leu Gln Val Phe Glu Ile
            180                 185                 190

Arg Ser Glu Lys Arg Trp Gln Asp Ile Ser Met Met Arg Met Lys Thr
        195                 200                 205

Ile Gly Glu His Ile Leu Ala His Ile Gln His Glu Val Asp Phe Leu
    210                 215                 220

Phe Cys Met Asp Val Asp Gln Val Phe Gln Asp Asn Phe Gly Val Glu
225                 230                 235                 240

Thr Leu Gly Gln Leu Val Ala Gln Leu Gln Ala Trp Trp Tyr Lys Ala
                245                 250                 255

Ser Pro Glu Lys Phe Thr Tyr Glu Arg Arg Glu Leu Ser Ala Ala Tyr
            260                 265                 270

Ile Pro Phe Gly Glu Gly Asp Phe Tyr Tyr His Ala Ala Ile Phe Gly
        275                 280                 285

Gly Thr Pro Thr His Ile Leu Asn Leu Thr Arg Glu Cys Phe Lys Gly
    290                 295                 300

Ile Leu Gln Asp Lys Lys His Asp Ile Glu Ala Gln Trp His Asp Glu
305                 310                 315                 320

Ser His Leu Asn Lys Tyr Phe Leu Phe Asn Lys Pro Thr Lys Ile Leu
                325                 330                 335

Ser Pro Glu Tyr Cys Trp Asp Tyr Gln Ile Gly Leu Pro Ser Asp Ile
            340                 345                 350

Lys Ser Val Lys Val Ala Trp Gln Thr Lys Glu Tyr Asn Leu Val Arg
```

355                 360                 365

Asn Asn Val
    370

<210> SEQ ID NO 5
<211> LENGTH: 368
<212> TYPE: PRT
<213> ORGANISM: Bos taurus

<400> SEQUENCE: 5

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Gly Gly Ser Ser Ile
        35                  40                  45

Gln Lys Gly Trp Trp Leu Pro Arg Trp Phe Asn Asn Gly Tyr His Glu
    50                  55                  60

Glu Asp Gly Asp Ile Asn Glu Glu Lys Glu Gln Arg Asn Glu Asp Glu
65                  70                  75                  80

Ser Lys Leu Lys Leu Ser Asp Trp Phe Asn Pro Phe Lys Arg Pro Glu
                85                  90                  95

Val Val Thr Met Thr Lys Trp Lys Ala Pro Val Val Trp Glu Gly Thr
            100                 105                 110

Tyr Asn Arg Ala Val Leu Asp Asn Tyr Tyr Ala Lys Gln Lys Ile Thr
        115                 120                 125

Val Gly Leu Thr Val Phe Ala Val Gly Arg Tyr Ile Glu His Tyr Leu
    130                 135                 140

Glu Glu Phe Leu Thr Ser Ala Asn Lys His Phe Met Val Gly His Pro
145                 150                 155                 160

Val Ile Phe Tyr Ile Met Val Asp Asp Val Ser Arg Met Pro Leu Ile
                165                 170                 175

Glu Leu Gly Pro Leu Arg Ser Phe Lys Val Phe Lys Ile Lys Pro Glu
            180                 185                 190

Lys Arg Trp Gln Asp Ile Ser Met Met Arg Met Lys Thr Ile Gly Glu
        195                 200                 205

His Ile Val Ala His Ile Gln His Glu Val Asp Phe Leu Phe Cys Met
    210                 215                 220

Asp Val Asp Gln Val Phe Gln Asp Lys Phe Gly Val Glu Thr Leu Gly
225                 230                 235                 240

Glu Ser Val Ala Gln Leu Gln Ala Trp Trp Tyr Lys Ala Asp Pro Asn
                245                 250                 255

Asp Phe Thr Tyr Glu Arg Arg Lys Glu Ser Ala Ala Tyr Ile Pro Phe
            260                 265                 270

Gly Glu Gly Asp Phe Tyr Tyr His Ala Ala Ile Phe Gly Gly Thr Pro
        275                 280                 285

Thr Gln Val Leu Asn Ile Thr Gln Glu Cys Phe Lys Gly Ile Leu Lys
    290                 295                 300

Asp Lys Lys Asn Asp Ile Glu Ala Gln Trp His Asp Glu Ser His Leu
305                 310                 315                 320

Asn Lys Tyr Phe Leu Leu Asn Lys Pro Thr Lys Ile Leu Ser Pro Glu
                325                 330                 335

Tyr Cys Trp Asp Tyr His Ile Gly Leu Pro Ala Asp Ile Lys Leu Val
            340                 345                 350

```
Lys Met Ser Trp Gln Thr Lys Glu Tyr Asn Val Val Arg Asn Asn Val
            355                 360                 365

<210> SEQ ID NO 6
<211> LENGTH: 370
<212> TYPE: PRT
<213> ORGANISM: Felis catus

<400> SEQUENCE: 6

Met Asn Val Lys Gly Arg Val Val Leu Ser Met Leu Val Val Ser Thr
1               5                   10                  15

Val Ile Val Val Phe Trp Glu Tyr Ile Asn Ser Pro Glu Gly Ser Phe
            20                  25                  30

Leu Trp Ile Tyr His Ser Lys Asn Pro Glu Val Gly Asp Ser Ser Thr
        35                  40                  45

Gln Lys Gly Trp Trp Phe Pro Ser Trp Phe Asn Asn Arg Thr His Ser
    50                  55                  60

Tyr Pro Glu Glu Glu Ala Val Asp Gly Asp Glu Gln Arg Lys Glu
65                  70                  75                  80

Asn Ser Glu Glu Leu Gln Leu Ser Asp Trp Phe Asn Pro Gln Lys Arg
                85                  90                  95

Pro Asp Val Val Thr Val Thr Glu Trp Lys Ala Pro Val Val Trp Glu
            100                 105                 110

Gly Thr Tyr Asn Lys Ala Ile Leu Glu Asn Tyr Tyr Ala Arg Gln Lys
        115                 120                 125

Ile Thr Val Gly Leu Thr Val Phe Ala Val Gly Arg Tyr Ile Glu His
    130                 135                 140

Tyr Leu Glu Glu Phe Leu Ile Ser Ala Asn Arg Tyr Phe Met Val Gly
145                 150                 155                 160

His Lys Val Ile Phe Tyr Ile Met Val Asp Asp Val Ser Lys Met Pro
                165                 170                 175

Leu Ile Glu Leu Gly Pro Leu Arg Ser Phe Lys Val Phe Glu Ile Lys
            180                 185                 190

Pro Glu Lys Arg Trp Gln Asp Ile Ser Met Met Arg Met Lys Ile Ile
        195                 200                 205

Gly Glu His Ile Val Ala His Ile Gln His Glu Val Asp Phe Leu Phe
    210                 215                 220

Cys Met Asp Val Asp Gln Val Phe Gln Asp Ser Phe Gly Val Glu Thr
225                 230                 235                 240

Leu Gly Gln Ser Val Ala Gln Leu Gln Ala Trp Trp Tyr Lys Ala Asp
                245                 250                 255

Pro Asp Glu Phe Thr Tyr Glu Arg Arg Lys Glu Ser Ala Ala Tyr Ile
            260                 265                 270

Pro Phe Gly Glu Gly Asp Phe Tyr Tyr His Ala Ala Ile Phe Gly Gly
        275                 280                 285

Thr Pro Thr Gln Val Leu Asn Ile Thr Gln Glu Cys Phe Lys Gly Ile
    290                 295                 300

Leu Gln Asp Lys Lys Asn Asp Ile Glu Ala Glu Trp His Asp Glu Ser
305                 310                 315                 320

His Leu Asn Lys Tyr Phe Leu Leu Asn Lys Pro Thr Lys Ile Leu Ser
                325                 330                 335

Pro Glu Tyr Cys Trp Asp Tyr His Ile Gly Leu Pro Ser Asp Ile Lys
            340                 345                 350

Ile Val Lys Ile Ser Trp Gln Thr Lys Glu Tyr Asn Leu Val Arg Asn
        355                 360                 365
```

Asn Ile
    370

<210> SEQ ID NO 7
<211> LENGTH: 369
<212> TYPE: PRT
<213> ORGANISM: Ovis aries

<400> SEQUENCE: 7

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Ser Gly Gly Ser Ser
        35                  40                  45

Ile Gln Lys Gly Trp Trp Phe Pro Arg Trp Phe Asn Asn Gly Tyr Gln
    50                  55                  60

Glu Glu Asp Glu Asp Val Asp Glu Glu Lys Gln Arg Lys Glu Asp
65                  70                  75                  80

Lys Ser Lys Leu Lys Leu Ser Asp Trp Phe Asn Pro Phe Lys Arg Pro
                85                  90                  95

Glu Val Val Thr Met Thr Asp Trp Lys Ala Pro Val Val Trp Glu Gly
            100                 105                 110

Thr Tyr Asn Arg Ala Val Leu Asp Tyr Tyr Ala Lys Gln Lys Ile
        115                 120                 125

Thr Val Gly Leu Thr Val Phe Ala Val Gly Arg Tyr Ile Glu His Tyr
    130                 135                 140

Leu Glu Glu Phe Leu Thr Ser Ala Asn Lys His Phe Met Val Gly His
145                 150                 155                 160

Arg Val Ile Phe Tyr Val Met Val Asp Asp Val Ser Arg Met Pro Leu
                165                 170                 175

Ile Glu Leu Gly Pro Leu Arg Ser Phe Lys Val Phe Glu Val Lys Pro
            180                 185                 190

Glu Arg Arg Trp Gln Asp Val Ser Met Val Arg Met Lys Thr Ile Gly
        195                 200                 205

Glu His Ile Val Ala His Ile Gln Arg Glu Val Asp Phe Leu Phe Cys
    210                 215                 220

Met Asp Val Asp Gln Val Phe Gln Asp Glu Phe Gly Val Glu Thr Leu
225                 230                 235                 240

Gly Glu Ser Val Ala Gln Leu Gln Ala Trp Trp Tyr Lys Ala Asp Pro
                245                 250                 255

Asp Glu Phe Thr Tyr Glu Arg Arg Lys Glu Ser Ala Ala Tyr Ile Pro
            260                 265                 270

Phe Gly Glu Gly Asp Phe Tyr Tyr His Ala Ala Ile Phe Gly Gly Thr
        275                 280                 285

Pro Thr Gln Val Leu Asn Ile Thr Gln Glu Cys Phe Lys Gly Ile Leu
    290                 295                 300

Lys Asp Lys Lys Asn Asp Ile Glu Ala Gln Trp His Asp Glu Ser His
305                 310                 315                 320

Leu Asn Lys Tyr Phe Leu Leu Asn Lys Pro Thr Lys Ile Leu Ser Pro
                325                 330                 335

Glu Tyr Cys Trp Asp Tyr His Ile Gly Leu Pro Ala Asp Ile Lys Leu
            340                 345                 350

Val Lys Met Ser Trp Gln Thr Lys Glu Tyr Asn Leu Val Arg Asn Asn

Val

<210> SEQ ID NO 8
<211> LENGTH: 337
<212> TYPE: PRT
<213> ORGANISM: Rattus norvegicus

<400> SEQUENCE: 8

Met Asn Val Lys Gly Lys Ile Ile Leu Ser Val Leu Met Val Ser Thr
 1               5                  10                  15

Val Leu Val Val Phe Trp Glu Tyr Val Asn Arg Thr His Ser Tyr Gln
                20                  25                  30

Glu Glu Asp Ile Glu Arg Ala Arg Glu Lys Gly Arg Asn Gly Asp Ser
            35                  40                  45

Ile Val Glu Pro Gln Leu Trp Asp Trp Phe Asn Pro Lys Asn Arg Pro
        50                  55                  60

Glu Val Leu Thr Val Thr Pro Trp Lys Ala Pro Ile Val Trp Glu Gly
65                  70                  75                  80

Thr Tyr Asp Thr Ala Leu Leu Glu Lys Tyr Tyr Ala Arg Gln Lys Ile
                85                  90                  95

Thr Val Gly Leu Thr Val Phe Ala Val Gly Lys Tyr Ile Glu His Tyr
            100                 105                 110

Leu Glu Asp Phe Leu Glu Ser Ala Asn Lys Tyr Phe Met Val Gly His
        115                 120                 125

Arg Val Ile Phe Tyr Val Met Met Asp Asp Thr Ser Arg Met Pro Ala
130                 135                 140

Val His Leu Ser Pro Leu His Ser Leu Gln Val Phe Glu Ile Arg Ser
145                 150                 155                 160

Glu Lys Arg Trp Gln Asp Ile Ser Met Met Arg Met Lys Thr Ile Gly
                165                 170                 175

Glu His Ile Leu Asp His Ile Gln His Glu Val Asp Phe Leu Phe Cys
            180                 185                 190

Met Asp Val Asp Gln Val Phe Gln Asp Asn Phe Gly Val Glu Thr Leu
        195                 200                 205

Gly Gln Leu Val Ala Gln Leu Gln Ala Trp Trp Tyr Lys Ala Ser Pro
210                 215                 220

Asp Glu Phe Thr Tyr Glu Arg Arg Glu Leu Ser Ala Ala Tyr Ile Pro
225                 230                 235                 240

Phe Gly Glu Gly Asp Phe Tyr Tyr His Ala Ala Val Phe Gly Gly Thr
                245                 250                 255

Pro Val His Ile Leu Asn Leu Thr Arg Glu Cys Phe Lys Gly Ile Leu
            260                 265                 270

Gln Asp Lys Lys His Asp Ile Glu Ala Gln Trp His Asp Glu Ser His
        275                 280                 285

Leu Asn Lys Tyr Phe Leu Phe Asn Lys Pro Thr Lys Ile Leu Ser Pro
290                 295                 300

Glu Tyr Cys Trp Asp Tyr His Ile Gly Leu Pro Ser Asp Ile Lys Asn
305                 310                 315                 320

Val Lys Ile Ala Trp Gln Thr Lys Glu Tyr Asn Leu Val Arg Ser Asn
                325                 330                 335

Val

<210> SEQ ID NO 9

```
<211> LENGTH: 371
<212> TYPE: PRT
<213> ORGANISM: Sus scrofa

<400> SEQUENCE: 9

Met Asn Val Lys Gly Arg Val Val Leu Ser Met Leu Val Leu Ser Thr
1               5                   10                  15

Val Met Val Val Phe Trp Glu Tyr Ile Asn Ser Pro Glu Gly Ser Leu
            20                  25                  30

Phe Trp Ile Tyr Gln Ser Lys Asn Pro Glu Val Gly Ser Ser Ala Gln
        35                  40                  45

Arg Gly Trp Trp Phe Pro Ser Trp Phe Asn Asn Gly Thr His Ser Tyr
    50                  55                  60

His Glu Glu Glu Asp Ala Ile Gly Asn Glu Lys Glu Gln Arg Lys Glu
65                  70                  75                  80

Asp Asn Arg Gly Glu Leu Pro Leu Val Asp Trp Phe Asn Pro Glu Lys
                85                  90                  95

Arg Pro Glu Val Val Thr Ile Thr Arg Trp Lys Ala Pro Val Val Trp
            100                 105                 110

Glu Gly Thr Tyr Asn Arg Ala Val Leu Asp Asn Tyr Tyr Ala Lys Gln
        115                 120                 125

Lys Ile Thr Val Gly Leu Thr Val Phe Ala Val Gly Arg Tyr Ile Glu
    130                 135                 140

His Tyr Leu Glu Glu Phe Leu Ile Ser Ala Asn Thr Tyr Phe Met Val
145                 150                 155                 160

Gly His Lys Val Ile Phe Tyr Ile Met Val Asp Asp Ile Ser Arg Met
                165                 170                 175

Pro Leu Ile Glu Leu Gly Pro Leu Arg Ser Phe Lys Val Phe Glu Ile
            180                 185                 190

Lys Ser Glu Lys Arg Trp Gln Asp Ile Ser Met Met Arg Met Lys Thr
        195                 200                 205

Ile Gly Glu His Ile Leu Ala His Ile Gln His Glu Val Asp Phe Leu
    210                 215                 220

Phe Cys Met Asp Val Asp Gln Val Phe Gln Asn Asn Phe Gly Val Glu
225                 230                 235                 240

Thr Leu Gly Gln Ser Val Ala Gln Leu Gln Ala Trp Trp Tyr Lys Ala
                245                 250                 255

His Pro Asp Glu Phe Thr Tyr Glu Arg Arg Lys Glu Ser Ala Ala Tyr
            260                 265                 270

Ile Pro Phe Gly Gln Gly Asp Phe Tyr Tyr His Ala Ala Ile Phe Gly
        275                 280                 285

Gly Thr Pro Thr Gln Val Leu Asn Ile Thr Gln Glu Cys Phe Lys Gly
    290                 295                 300

Ile Leu Gln Asp Lys Glu Asn Asp Ile Glu Ala Glu Trp His Asp Glu
305                 310                 315                 320

Ser His Leu Asn Lys Tyr Phe Leu Leu Asn Lys Pro Thr Lys Ile Leu
                325                 330                 335

Ser Pro Glu Tyr Cys Trp Asp Tyr His Ile Gly Met Ser Val Asp Ile
            340                 345                 350

Arg Ile Val Lys Ile Ala Trp Gln Lys Lys Glu Tyr Asn Leu Val Arg
        355                 360                 365

Asn Asn Ile
    370
```

<210> SEQ ID NO 10
<211> LENGTH: 23
<212> TYPE: PRT
<213> ORGANISM: Flu virus M2e

<400> SEQUENCE: 10

Ser Leu Leu Thr Glu Val Glu Thr Pro Ile Arg Asn Glu Trp Gly Ser
1               5                   10                  15

Arg Ser Asn Asp Ser Ser Asp
            20

<210> SEQ ID NO 11
<211> LENGTH: 69
<212> TYPE: DNA
<213> ORGANISM: Flu virus M2e

<400> SEQUENCE: 11
agtcttctaa ccgaggtcga aacgcttatc agaaacgaat ggggggtgcag atgcaacggt      60 tcaagtgat                                                              69

<210> SEQ ID NO 12
<211> LENGTH: 28
<212> TYPE: PRT
<213> ORGANISM: Artificial Sequence
<220> FEATURE:
<223> OTHER INFORMATION: Synthetic

<400> SEQUENCE: 12

Gly Gly Gly Asn Gly Ser Gly Gly Asn Gly Thr Gly Gly Gly Asn
1               5                   10                  15

Gly Ser Gly Gly Gly Asn Gly Thr Gly Gly Gly Ser
            20                  25

<210> SEQ ID NO 13
<211> LENGTH: 337
<212> TYPE: PRT
<213> ORGANISM: Mus musculus

<400> SEQUENCE: 13

Met Asn Val Lys Gly Lys Val Ile Leu Leu Met Leu Ile Val Ser Thr
1               5                   10                  15

Val Val Val Val Phe Trp Glu Tyr Val Asn Arg Thr His Ser Tyr Gln
                20                  25                  30

Glu Asp Asn Val Glu Gly Arg Arg Glu Lys Gly Arg Asn Gly Asp Arg
            35                  40                  45

Ile Glu Glu Pro Gln Leu Trp Asp Trp Phe Asn Pro Lys Asn Arg Pro
        50                  55                  60

Asp Val Leu Thr Val Thr Pro Trp Lys Ala Pro Ile Val Trp Glu Gly
65                  70                  75                  80

Thr Tyr Asp Thr Ala Leu Leu Glu Lys Tyr Tyr Ala Thr Gln Lys Leu
                85                  90                  95

Thr Val Gly Leu Thr Val Phe Ala Val Gly Lys Tyr Ile Glu His Tyr
            100                 105                 110

Leu Glu Asp Phe Leu Glu Ser Ala Asp Met Tyr Phe Met Val Gly His
        115                 120                 125

Arg Val Ile Phe Tyr Val Met Ile Asp Asp Thr Ser Arg Met Pro Val
130                 135                 140

Val His Leu Asn Pro Leu His Ser Leu Gln Val Phe Glu Ile Arg Ser
145                 150                 155                 160

-continued

```
Glu Lys Arg Trp Gln Asp Ile Ser Met Met Arg Met Lys Thr Ile Gly
                165             170             175

Glu His Ile Leu Ala His Ile Gln His Glu Val Asp Phe Leu Phe Cys
            180             185             190

Met Asp Val Asp Gln Val Phe Gln Asp Asn Phe Gly Val Glu Thr Leu
        195             200             205

Gly Gln Leu Val Ala Gln Leu Gln Ala Trp Trp Tyr Lys Ala Ser Pro
    210             215             220

Glu Lys Phe Thr Tyr Glu Arg Arg Glu Leu Ser Ala Ala Tyr Ile Pro
225             230             235             240

Phe Gly Glu Gly Asp Phe Tyr Tyr His Ala Ala Ile Phe Gly Gly Thr
                245             250             255

Pro Thr His Ile Leu Asn Leu Thr Arg Glu Cys Phe Lys Gly Ile Leu
            260             265             270

Gln Asp Lys Lys His Asp Ile Glu Ala Gln Trp His Asp Glu Ser His
        275             280             285

Leu Asn Lys Tyr Phe Leu Phe Asn Lys Pro Thr Lys Ile Leu Ser Pro
    290             295             300

Glu Tyr Cys Trp Asp Tyr Gln Ile Gly Leu Pro Ser Asp Ile Lys Ser
305             310             315             320

Val Lys Val Ala Trp Gln Thr Lys Glu Tyr Asn Leu Val Arg Asn Asn
                325             330             335

Val
```

US 9,662,383 B2

COMPOSITIONS AND METHODS FOR INCREASING IMMUNOGENICITY OF GLYCOPROTEIN VACCINES

PRIORITY STATEMENT

This application for patent is the national stage entry of, and claims priority under 35 USC 111(a) to, PCT Application No. PCT/US2008/004020, filed on Mar.26, 2008, now abandoned, which claims priority to U.S. Provisional Application Ser. No. 60/920,221, filed on Mar. 26, 2007, now abandoned, the disclosure of each of which is herein incorporated by reference in its entirety.

FIELD OF THE INVENTION

The present invention relates to the field of microbial vaccines such as influenza virus vaccines. In particular, the present invention provides methods and compositions related to flu virus and flu virus immunogens that comprise α-gal epitopes (Galα1-3Galβ1-4(3)GlcNAc-R).

BACKGROUND OF THE INVENTION

Influenza (flu) is a contagious respiratory disease caused by influenza virus infection. Annual flu outbreaks in the United States affect 5-20% of the population (*CDC Fact Sheet*, 2006). Flu complications such as bacterial pneumonia, ear and/or sinus infections, dehydration and worsening of chronic medical conditions can result in severe illness and even death. Yearly flu vaccinations are recommended for preventing the flu, particularly for high-risk individuals (e.g., children, elderly, etc.) and their caretakers (e.g., health care workers).

Currently used inactivated influenza (flu) virus vaccines are the product of the 6+2 re-assortment containing hemagglutinin (HA) and neuraminidase (NA) genes from the vaccine target strain and the remaining genes from A/Puerto Rico/8/34-H1N1 (PR8). These vaccines display suboptimal efficacy as determined by the finding that approximately 25%-50% of immunized individuals (in particular elderly populations) contract the disease during the flu season (*Webster, Vaccine,* 18:1686, 2000). The need for increasing immunogenicity of flu vaccines is an urgent matter because of the risk for pandemic outbreaks of the H5N1 avian influenza virus. The avian flu virus causes severe and often fatal disease in humans characterized by fulminant pneumonia and multi-organ failure (De Jong et al., *Nat Med,* 12:1203, 2006). The virus displays high replication efficacy, broad tissue tropism and systemic replication, which is likely associated with the high virulence of this virus (De Jong et al., supra, 2006). The avian flu virus has caused the recently documented human H5N1 infections. However, there is a significant risk that additional mutations in H5N1 will convert the virus into an infectious form able to spread from human to human. Therefore, the development of an effective prophylactic vaccine against both the seasonal infectious wild type virus and the H5N1 avian virus is needed to prevent future pandemics.

Based on a wide body of research that has been performed on flu vaccines it has been determined that an effective flu vaccine, will have to achieve several immunological goals including: 1) eliciting an anti-HA reactive antibody response to prevent infection of cells (including respiratory tract cells) by the pathogenic virus; and 2) eliciting a broad cross-protective antibody response against the conserved M2e ectodomain of the ion channel M2 protein for inducing antibody mediated destruction of infected cells expressing large amounts of the M2 protein; and 3) eliciting a broad cross-protective cellular immune response against flu virus nucleoprotein (NP) for including cytotoxic T cells (CTL) mediated destruction of infected cells presenting NP peptides (Black et al., *J Gen Virol,* 74:143-146, 1993; and Flynn et al., *Proc Natl Acad Sci USA,* 96:8597, 1999). The broad immune response to M2e and to NP is feasible since these proteins are conserved in various flu virus strains, unlike HA which differs significantly in different strains (Black et al., supra, 1993; and Riberdy et al., *J Virol,* 73:1453, 1999). Since the M2 protein is present in only small amounts in subunit vaccines (Zhang et al., *Mol Immunol,* 43: 2195, 2006), and since NP is non-immunogenic in subunit vaccines, the immunogenicity of recombinant M2e and NP has been found to be suboptimal (Mozdzanowska et al., *Vaccine,* 21: 2616, 2003). Such low immunogenicity is usually associated with poor uptake of the vaccine by antigen presenting cells (APC) at the inoculation site.

Thus, compositions and methods for increasing the immunogenicity of inactivated flu virus are needed in the art. Likewise, compositions and methods for increasing the immunogenicity of other microbial antigens are desirable.

SUMMARY OF THE INVENTION

The present invention relates to the field of microbial vaccines in general and influenza virus vaccines in particular. In one embodiment, the present invention provides compositions and methods for propagating influenza virus in, for example, human, ape, old world monkey or bird cells that have been engineered to express an α1,3galactosyltransferase (α1,3GT) gene to produce virions bearing α-gal epitopes (Galα1-3Galβ1-4(3)GlcNAc-R). Administration of influenza virus bearing α-gal epitopes to a subject results in enhanced targeting of the virions to antigen presenting cells resulting in a heightened humoral and cellular immune response to influenza. In another embodiment, the present invention provides fusion proteins between influenza virus hemagglutinin (HA) and a microbial peptide or protein of interest, and enzymatic processing of this fusion protein to carry α-gal epitopes, to increase the immunogenicity of the microbial peptide or protein of interest.

The present invention provides methods comprising: providing an influenza virus and a host cell susceptible to infection by the influenza virus and comprising an expression vector comprising a nucleic acid encoding an α1,3galactosyltransferase (α1,3gal) in operable combination with a promoter; and inoculating the host cell to produce an inoculated host cell, wherein the inoculated host cell produces an influenza virus bearing an α-gal epitope (Galα1-3Galβ1-4 (3)GlcNAc-R). In some embodiments, the influenza virus is an influenza A virus or an influenza B virus. In some embodiments, the host cell is selected from the group consisting of a human cell, an ape cell, an Old World monkey cell and a bird cell. In some preferred embodiments, the Old World monkey cell is a Vero cell. In other embodiments, the host cell is a New World monkey cell or a non-primate mammalian cell. In some preferred embodiments, the non-primate mammalian cell is a MDCK cell or a NIH/3T3 cell. In some embodiments, the α1,3gal is an enzyme of a species selected from the group consisting of a mouse, a cow, a cat, a sheep, a rat, a pig and a New World monkey. In some preferred embodiments, the New World monkey is a common marmoset. In some preferred embodiments, the methods further comprise inactivating the influenza virus bearing an α-gal epitope to produce an inactivated influenza virus bearing an α-gal epitope. In additional embodiments, the methods further comprise administering the inactivated influenza virus bearing an α-gal epitope to a subject having anti-Gal antibodies under conditions suitable for induction of an immune response by the subject. In some embodiments, the subject is selected from the group consisting of humans, apes, Old World monkeys and birds. In some embodiments, the immune response comprises one or both of production of antibodies reactive with the influenza virus and T lymphocytes reactive with cells infected by the influenza virus. In some preferred embodiments, the administering is such that the subject's susceptibility to developing symptoms of influenza virus infection is reduced.

Additionally, the present invention provides compositions comprising an isolated host cell susceptible to infection by an influenza virus and comprising an expression vector comprising a nucleic acid encoding an α1,3galactosyltransferase (α1,3gal) in operable combination with a promoter. In some preferred embodiments, the isolated host cell has little or no sialyltransferase activity. In some embodiments, the isolated host cell is an inoculated host cell that produces an influenza virus bearing an α-gal epitope (Galα1-3Galα1-4(3)GlcNAc-R). In some embodiments, the influenza virus is an influenza A virus or an influenza B virus. In some embodiments, the host cell is selected from the group consisting of a human cell, an ape cell, an Old World monkey cell and a bird cell. In some preferred embodiments, the Old World monkey cell is a Vero cell. In other embodiments, the host cell is a New World monkey cell or a non-primate mammalian cell. In some preferred embodiments, the non-primate mammalian cell is a MDCK cell or a NIH/3T3 cell. In some embodiments, the α1,3gal is an enzyme of a species selected from the group to consisting of a mouse, a cow, a cat, a sheep, a rat, a pig and a New World monkey. In some preferred embodiments, the New World monkey is a common marmoset.

The present invention also provides methods comprising producing a fusion protein comprising an amino-terminal portion and a carboxy-terminal portion, wherein the amino-terminal portion comprises a glycoprotein with two or more carbohydrate chains bearing α-gal epitopes (Galα1-3Galβ(1-4(3)GlcNAc-R) and the carboxy-terminal portion comprises a protein antigen of interest. Moreover the present invention provides compositions comprising a fusion protein comprising an amino-terminal portion and a carboxy-terminal portion, wherein the amino-terminal portion comprises a glycoprotein with two or more carbohydrate chains bearing α-gal epitopes (Galα1-3Galβ1-4(3)GlcNAc-R) and the carboxy-terminal portion comprises a protein antigen of interest.

The present invention provides methods of producing an isolated fusion protein comprising an amino-terminal portion and a carboxy-terminal portion, the method comprising: providing recombinant host cells comprising an expression vector, wherein the expression vector comprises a nucleic acid encoding the fusion protein in operable combination with a promoter, and wherein the amino-terminal portion comprises influenza virus hemagglutinin (HA) and the carboxy-terminal portion comprises a protein antigen of interest; culturing the recombinant host cells to produce the fusion protein; and isolating the fusion protein. In some embodiments, the influenza virus is an influenza A virus or an influenza B virus. In some preferred embodiments, the amino-terminal portion comprises an extracellular domain of HA in the absence of transmembrane and cytoplasmic domains of HA. In some preferred embodiments, the protein antigen of interest comprises an influenza virus nucleoprotein or an influenza virus M2e oligopeptide. In some embodiments, the protein antigen of interest is of a microbial pathogen selected from the group consisting of a virus, a bacterium, a parasite and a fungus. In some preferred embodiments, the methods further comprise incubating the fusion protein in the presence of neuraminidase, α1,3 galactosyltransferase (α1,3gal) and UDP-galactose to produce a fusion protein comprising α-gal epitopes. In some embodiments, the neuraminidase is derived from Vibrio cholera. In some embodiments, the α1,3galactosyltransferase (α1,3gal) is a recombinant marmoset enzyme. In some preferred embodiments, the transgenic host cell further comprises an expression vector comprising a nucleic acid encoding influenza virus neuraminidase in operable combination with a promoter to effect removal of sialic acid from the fusion protein to produce a sialic acid deficient fusion protein. In some embodiments, the methods further comprise incubating the sialic acid deficient fusion protein in the presence of α1,3galactosyltransferase (α1,3gal) and UDP-galactose to produce a fusion protein comprising α-gal epitopes. In some embodiments, the transgenic host cell further comprises an expression vector comprising a nucleic acid encoding an α1,3galactosyltransferase (α1,3gal) in operable combination with a promoter to produce a fusion protein comprising α-gal epitopes. In some embodiments, the methods further comprise administering the fusion protein comprising α-gal epitopes to a subject having anti-Gal antibodies under conditions suitable for induction of an immune response by the subject. In some embodiments, the subject is selected from the group consisting of humans, apes, old world monkeys and birds. In some embodiments, the immune response comprises production of antibodies reactive with the fusion protein and T lymphocytes reactive with antigen presenting cells pulsed with the fusion protein. In some embodiments, the administering is such that the subject's susceptibility to developing symptoms of influenza virus infection is reduced. Also provided are fusion proteins produced by the above methods.

Additionally, the present invention provides compositions comprising a fusion protein comprising an amino-terminal portion and a carboxy-terminal portion, wherein the amino-terminal portion comprises an influenza virus hemagglutinin (HA) and the carboxy-terminal portion comprises a protein antigen of interest. In some preferred embodiments, the HA bears α-gal epitopes. In some embodiments, the protein antigen of interest does not bear α-gal epitopes. In some embodiments, the HA is of an influenza A virus or an influenza B virus. In some preferred embodiments, the HA is of an avian influenza virus.

Figure 1:
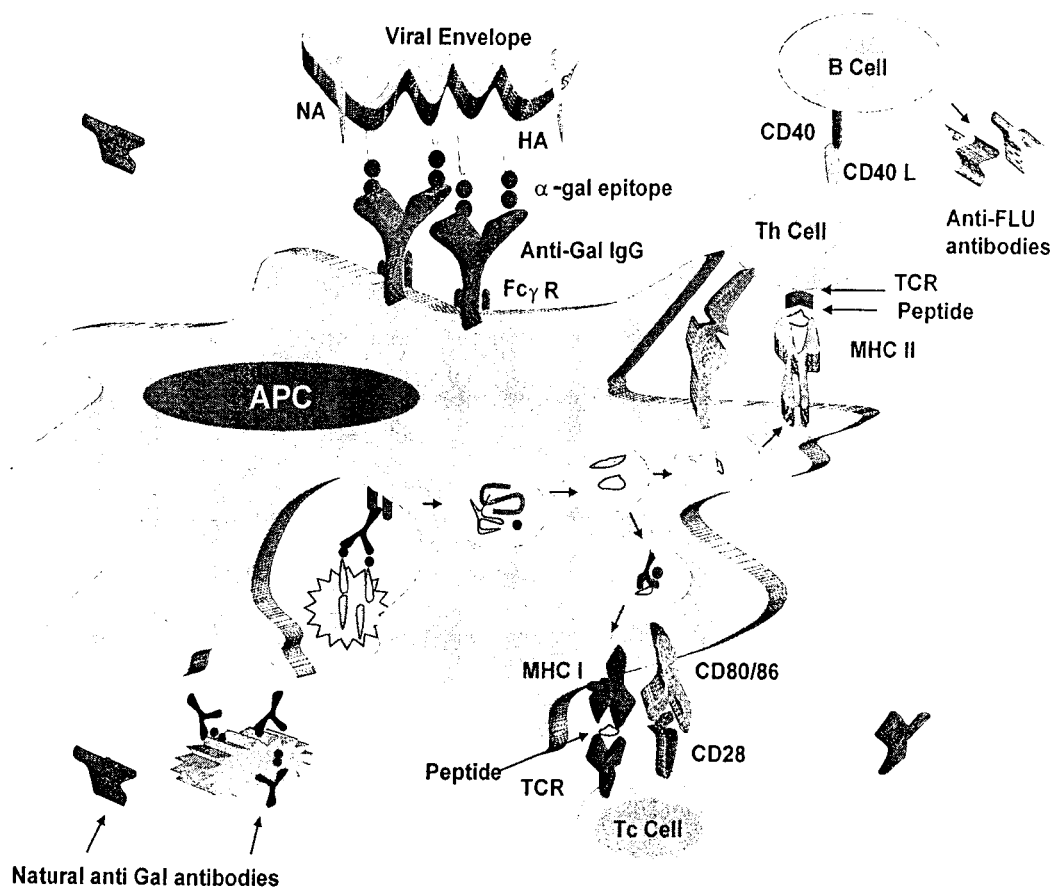
FIG. 1 illustrates an exemplary embodiment of the present invention comprising anti-Gal mediated targeting of flu$_{\alpha gal}$ virus vaccine (propagated in Vero$_{\alpha GT}$ cells) to antigen presenting cells (APC). Nonetheless, knowledge of the mechanism(s) involved is not necessary in order to make and use the present invention. Inactivated flu virus with α-gal epitopes (dark dots) is injected into a vaccine recipient. Anti-Gal binds to the α-gal epitopes on the virus and opsonizes it. The Fc portion of anti-Gal interacts with Fcγ receptors (FcγR) on APC and induces the uptake of the vaccine by the APC. The internalized virus undergoes processing in the endocytic vesicles and in the cytoplasm. The viral immunogenic peptides are presented on MHC class I molecules for the activation of CD8+ CTL precursors (T$_C$ cells), and on MHC class II molecules for the activation of helper T cells ($T_H$ cells). This activation is also facilitated by signal 2 (e.g., co-stimulation) provided by the APC (CD28 interacting with CD80/86). Activated $T_H$ cells provide help for the antibody response by B cells and for CTL activation. Activated $T_C$ cells differentiate into CTL that kill virus infected cells. This mechanism of anti-Gal mediated targeting of vaccines is applicable also for recombinant fusion proteins such as $HA_{\alpha gal}$-M2e and $HA_{\alpha gal}$-NP, in which anti-Gal binds to α-gal epitopes on the ≥6 carbohydrate chains of the HA portion of the fusion protein and thus targets the vaccinating fusion glycoprotein to the APC. Again, knowledge of the mechanism(s) involved is not necessary in order to make and use the present invention.

FIG. 2 shows the synthesis of α-gal epitopes on the influenza virus HA glycoprotein. HA of influenza virus produced in mammalian cells has at least 6 N (asparagine)-linked carbohydrate chains as shown on the left carbohydrate chain. The sialic acid (SA) residues capping the N-linked carbohydrate chains (left chain) are removed (e.g., desialylated) by neuraminidase (middle chain). The α-gal epitopes (Galα1-3Galβ1-4GlcNAc-R) are synthesized by the linking of galactose (Gal) from the sugar donor uridine diphosphate galactose (UDP-GAL), to the exposed N-acetyllactosamines (Galβ1(31-4GlcNAc-R) residues as a result of the catalytic activity of recombinant α1,3galactosyltransferase (α1,3GT). These α-gal epitopes of the HA portion of the vaccinating fusion proteins $HA_{\alpha gal}$-M2e and $HA_{\alpha gal}$-NP when administered to a subject readily bind in situ to natural anti-Gal IgG molecules (illustrated as a schematic IgG molecule), forming immune complexes that target HA to APC.

FIG. 3A shows the expression of α-gal epitopes on HA of $PR8_{\alpha gal}$ as demonstrated by Western blots stained with serum anti-Gal purified from α1,3GT knockout (KO) mouse serum, and with anti-Gal M86 mAb. FIG. 3B shows the binding of anti-Gal M86 mAb to α-gal epitopes expressed on $PR8_{\alpha gal}$ virus attached to microtiter plate wells as determined by ELISA. Open triangles represent unprocessed PR8 virus, open squares represent PR8 virus incubated with inactivated recombinant α1,3GT, while open circles represent $PR8_{\alpha gal}$ virus generated by incubation of PR8 with active recombinant α1,3GT.

FIG. 4 provides the results of an ELISPOT analysis for IFNγ secretion in mice injected with PR8 or $PR8_{\alpha gal}$. The spleen lymphocytes were obtained 4 weeks after the second injection of inactivated $PR8_{\alpha gal}$ virus, or PR8 virus (1 μg in Ribi adjuvant) and were co-incubated for 24 h with dendritic cells (DC) pre-pulsed with PR8 virus. The lymphocytes were incubated in ELISPOT wells coated with anti-IFNγ antibody and thus the spots in each well represent IFNγ secreting T cells. The lymphocytes were tested in the presence of PR8 pulsed DC (dark columns), or with control DC that were not pulsed with PR8 (light columns). Data is shown as the mean±standard deviation of spots/$10^6$ cells from triplicate wells.

FIG. 5 shows the intracytoplasmic cytokine staining for IFNγ in CD8+ (A) and CD4+ T cells (B) in PR8 or $PR8_{\alpha gal}$ immunized mice. The spleen lymphocytes were obtained 4 weeks after the second injection of inactivated $PR8_{\alpha gal}$ virus, or PR8 virus (1 μg in Ribi adjuvant) and were co-incubated for 24 h with dendritic cells (DC) pre-pulsed with PR8 virus. The lymphocytes from 6 mice in each group were double stained for intracytoplasmic IFNγ and for the CD8 or CD4 membrane markers.

FIG. 6 graphically depicts the production of anti-PR8 antibodies in mice immunized with 1 μg inactivated $PR8_{\alpha gal}$ (○), or with 1 μg inactivated PR8 (○) in Ribi adjuvant. FIG. 6A shows the anti-PR8 IgG response in KO mice (n=6 per group). FIG. 6B shows the anti-PR8 IgG response in wild type (WT) mice (n=6 per group). FIG. 6C shows the anti-PR8 IgA response in KO mice (n=6 per group).

FIG. 7 compares the survival of mice immunized with inactivated PR8 (○) or with inactivated $PR8_{\alpha gal}$ (○) and challenged intranasally with 2000 PFU (plaque forming units) of live PR8 in 50 μl (n=26/group). The data are presented as the percentage of mice surviving the viral challenge, which did not change after day 15 post-challenge.

FIG. 8 shows the steps involved in the production of a HA-M2e fusion protein. The gene of the fusion protein HA-M2e is generated by PCR as follows. 1) The HA gene (without the transmembrane and cytoplasmic regions) is amplified with a downstream (3') primer that includes sequences encoding M2e, encoding three glycines (as a linker) and 15 nucleotides of the 3' domain of the HA gene (but not including the HA stop codon). 2) The resulting PCR product of step 1 including the HA gene and the additional sequence of M2e (dotted lines) is mixed with a 3' primer of M2e, a tag of 6 histidines ($His_6$), a stop codon and a restriction site. The 5' primer is that of HA containing a restriction site, which is different than that in the 3' region. 3) The resulting gene contains HA fused to M2e via a $Gly_3$ linker, as well as a C-terminal $His_6$ tag. This gene is inserted into a vector used for transfection and expression of the gene in mammalian cells for in vitro or in vivo expression of the recombinant gene.

FIG. 9 shows the steps involved in the production of a HA-NP fusion protein. The gene of the fusion protein HA-NP is generated by PCR as follows. 1) The HA gene (without the transmembrane and cytoplasmic regions) is amplified with a downstream (3') primer that includes sequences encoding 3 glycines (as a linker). The NP sequence is amplified with a 5' sequence encoding 3 glycines and the 3' sequence of HA (but not including the HA stop codon). 2) The resulting PCR products of step 1 including the HA gene and the sequence of NP (dotted lines) is mixed with a 3' primer of NP (but not including the NP stop codon), a tag of 6 histidines ($His_6$), a stop codon and a restriction site. The 5' primer is that of HA containing a restriction site, which is different from that in the 3' region. In the initial cycles of this PCR, the NP gene (previously amplified by PCR) serves as a 3' primer for the HA sequence, while the HA gene (previously amplified by PCR) serves as a 5' primer for NP (small arrows). Once the full length HA-NP fused gene is synthesized, it is further amplified by the 5' HA and 3' NP (+$His_6$+ stop codon) primers containing the restriction sites. 3) The resulting gene contains HA fused to NP via the $Gly_3$ linker, as well as a C-terminal $His_6$ tag. This gene is inserted into a vector used for transfection and expression of the gene in mammalian cells for in vitro or in vivo expression of the recombinant gene.

FIG. 10A provides a nucleic acid sequence of an exemplary marmoset α1,3galactosyltransferase (SEQ ID NO:1), while FIG. 10B provides the corresponding amino acid sequence (SEQ ID NO:2).

FIG. 11A provides a nucleic acid sequence of an exemplary mouse α1,3galactosyltransferase (SEQ ID NO:3), while FIG. 11B provides the corresponding amino acid sequence (SEQ ID NO:4).

FIG. 12 provides a ClustalW alignment of α1,3galactosyltransferase amino acid sequences of marmoset (SEQ ID NO:2), mouse (SEQ ID NO:4), cow (SEQ ID NO:5), cat (SEQ ID NO:6), sheep (SEQ ID NO:7), rat (SEQ ID NO:8) and pig (SEQ ID NO:9). The alignment is generated from scores calculated as described (Wilbur and Lipman, *Proc*

*Natl Acad Sci USA*, 80:726-730, 1983; and Myers and Miller, *Comput Applic Biosci*, 4:11-17, 1988).

DEFINITIONS

To facilitate an understanding of the present invention, a number of terms and phrases are defined below:

The term "α-gal epitope" as used herein, refers to any molecule, or part of a molecule, with a terminal structure comprising Galα1-3Galβ1-4GlcNAc-R, Galα1-3Galβ1-3GlcNAc-R, or any carbohydrate chain with terminal Galα1-3Gal at the non-reducing end.

The term "glycolipid" as used herein, refers to any molecule with at least one carbohydrate chain linked to a ceramide, a fatty acid chain, or any other lipid. Alternatively, a glycolipid maybe referred to as a glycosphingolipid.

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide. For instance the term "HA gene" encompasses the full-length HA nucleotide sequence. However, it is also intended that the term encompass fragments of the HA nucleotide sequence, as well as other domains (e.g., functional domains) within the full-length HA nucleotide sequence. Furthermore, the terms "HA gene," "HA nucleotide sequence," and "HA polynucleotide sequence" encompass DNA, cDNA, and RNA sequences.

As used herein, "homology" refers to sequence similarity or identity as determined using standard techniques known in the art (See e.g., Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid. Res, 12:387-395, 1984). Sequence similarity determinations are made in part through aligning sequences. A commonly used alignment method is BLAST, although there are other methods that also find use in aligning sequences (Altschul et al., J Mol Biol, 215:403-410, 1990; and Karlin et al., Proc Natl Acad Sci USA, 90:5873-5787, 1993). A particularly useful BLAST program is the WU-BLAST-2 program (See, Altschul et al., Meth Enzymol, 266:460-480, 1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A percent amino acid sequence identity value is determined by the number of matching identical residues divided by the total number of residues of the longer sequence in the aligned region. The longer sequence is the one having the most actual residues in the aligned region (gaps introduced by WU-Blast-2 to maximize the alignment score are ignored). Likewise, percent (%) nucleic acid sequence identity is defined as the percentage of nucleotide residues in a candidate sequence that are identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, the term "purified" refers to molecules (polynucleotides or polypeptides) that are removed from their natural environment, isolated or separated. "Substantially purified" molecules are at least 50% free, preferably at least 75% free, more preferably at least 90% and most preferably at least 95% free from other components with which they are naturally associated. Similarly, the term "isolated" as used herein, refers to any composition or mixture that has undergone a laboratory purification procedure including, but not limited to, extraction, centrifugation and chromatographic separation (e.g., thin layer chromatography or high performance liquid chromatography). Usually such a purification procedures provides an isolated composition or mixture based upon physical, chemical, or electrical potential properties. Depending upon the choice of procedure an isolated composition or mixture may contain other compositions, compounds or mixtures having similar chemical properties.

The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal) or may provide a tool for isolation purposes (e.g. GST).

The terms "alpha-1,3-galactosyltransferase," "α1,3GT," "glycoprotein alpha-galactosyltransferase 1" and "GGTA1," as used herein refer to any enzyme capable of synthesizing α-gal epitopes. The enzyme is expressed in most mammals with the exception of humans, apes and Old World monkeys. The carbohydrate structure produced by the enzyme is immunogenic in man and most healthy people have high titer natural anti α-gal antibodies. In some embodiments, the term "α1,3GT" refers to a common marmoset gene (e.g., *Callithrix jacchus*—GENBANK Accession No. S71333) and its gene product, as well as its functional mammalian counterparts (e.g., other New World monkeys, prosimians and non-primate mammals, but not Old World monkeys, apes and humans). The marmoset α1,3GT coding region is set forth as SEQ ID NO:1, while the marmoset α1,3GT protein sequence is set forth as SEQ ID NO:2. Moreover, the mouse α1,3GT coding sequence is set forth as SEQ ID NO:3 (e.g., *Mus musculus*—nucleotides 445 to 1560 of GEN-BANK Accession No. NM 010283), while the mouse α1,3GT protein sequence is set forth as SEQ ID NO:4. Other non-primate mammalian α1,3GT enzymes include but are not limited to bovine α1,3GT (e.g., *Bos taurus*—GEN-BANK Accession No. NM_177511), feline α1.3GT (e.g., *Felis catus*—GENBANK Accession No. NM_001009308), ovine α1,3GT (e.g., *Ovis aries*—GENBANK Accession No. NM_001009764), rat α1,3GT (e.g., *Rattus norvegicus*—GENBANK Accession No. NM_145674) and porcine α1,3GT (e.g., *Sus scrofa*—GENBANK Accession No. NM 213810). Some embodiments of the present invention comprise a functional variant of a mammalian α1,3GT, which differs from the wild type mammalian α1,3GT sequences in, for example, fewer than 1-5% of the residues. In particular, α1,3GT variants include but are not limited to naturally occurring functional mammalian α1,3GT variants, as well as non-naturally occurring variants generated by recombinant or other means (e.g., 1, 2, 3, 4 or 5 amino acid substitutions, deletions, or additions, preferably corresponding to a residue from a functional mammalian α1,3GT homolog) are contemplated to find use in the compositions and methods of the present invention. In other embodiments, truncated forms of a mammalian α1,3GT, which retain catalytic activity, are employed (e.g., GGTA 1 lacking 90 amino acid N-terminal stem region).

The term "anti-Gal binding epitope", as used herein, refers to any molecule or part of molecule that is capable of binding in vivo the natural anti-Gal antibody.

The term "vaccine" as used herein, refers to a composition that is administered to produce or artificially increase an immune response to an immunogen. For example, "vaccine compositions" frequently comprise a preparation of killed or live attenuated microorganisms. Alternatively, subunit vaccines frequently comprise a preparation of isolated nucleic acids or proteins corresponding to the genes or gene products of a microorganism of interest.

The term "route" as used herein, refers to methods for administration of a prophylactic or therapeutic agent. In some embodiments, "route" refers to the method of administration of a vaccine including but not limited to intramuscular, intravenous, intraperitoneal, subcutaneous, oral, intranasal, intravaginal, intrarectal, and stomacheal administration methods.

As used herein, the term "physiologically acceptable solution" refers to an isotonic solution such as an aqueous solution comprising for example, saline, phosphate buffered saline, Hanks' solution, or Ringer's solution.

As used herein, the term "immune response" refers to the reactivity of a subject's immune system in response to an antigen. In mammals, this may involve antibody production, induction of cell-mediated immunity, and/or complement activation. The term immune response encompasses but is not limited to one or more of a "lymphocyte proliferative response," a "cytokine response," an "antibody response," and a "cytotoxic T lymphocyte response."

The term "reactive with an antigen of interest" when made in reference to an immune response refers to an increased level of the immune response to the antigen of interest (e.g., flu virus) as compared to the level of the immune response to a control (e.g., irrelevant antigen).

The term "lymphocyte proliferative response" refers to antigen-induced increase in lymphocyte numbers. Alternatively, or in addition, the term "proliferation" refers to the physiological and morphological progression of changes that cells undergo when dividing, for instance including DNA replication as measured by tritiated thymidine incorporation.

The term "cytokine response" refers to antigen-induced cytokine secretion by lymphocytes as measured for instance by assaying culture supernatants for cytokine content (e.g., IL-2, IFNγ, TNFα, IL-4, etc) by ELISA.

The term "antibody response" refers to the production of antibodies (e.g., IgM, IgA, IgG) that bind to an antigen of interest (e.g., flu virus), this response is measured for instance by assaying sera by ELISA.

As used herein, the term "antibodies reactive with" refers to antibodies that bind to an antigen of interest. In preferred embodiments, the term "antibodies reactive with" is used in reference to antibodies that bind to a virus of interest (or to a viral protein).

The term "cytotoxic T lymphocytes reactive with" refers to cytotoxic T lymphocytes capable of lysing an MHC (e.g., HLA)-matched cell presenting epitopes derived from an antigen of interest. In preferred embodiments, the term "cytotoxic T lymphocytes reactive with" is used in reference to cytotoxic T lymphocytes or CTLs capable of lysing a MHC-matched cell infected by a virus of interest, or presenting epitopes derived from viral proteins.

The term "helper T lymphocytes reactive with" refers to helper T lymphocytes capable of secreting lymphokines in response to an MHC (e.g., HLA)-matched cell presenting epitopes derived from an antigen of interest. In preferred embodiments, the term "helper T lymphocytes reactive with" is used in reference to helper T lymphocytes or $T_H$ cells capable of secreting lymphokines in response to an MHC-matched cell infected by the virus of interest, or presenting epitopes derived from viral proteins.

The term "adjuvant" as used herein refers to any compound that when injected together with an antigen, non-specifically enhances the immune response to that antigen. Exemplary adjuvants include but are not limited to incomplete Freunds adjuvant (IFA), aluminum-based adjuvants (e.g., AIOH, AIPO4, etc), and Montanide ISA 720.

The terms "excipient," "carrier" and "vehicle" as used herein refer to usually inactive accessory substances into which a pharmaceutical substance (e.g., inactivated flu virus) is suspended. Exemplary carriers include liquid carriers (such as water, saline, culture medium, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins).

The terms "mammals" and "mammalian" refer to animals of the class mammalian that nourish their young by fluid secreted from mammary glands of the mother, including human beings. The class "mammalian" includes placental animals, marsupial animals, and monotrematal animals.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to animals, which receive a mock treatment (e.g., inactivated flu virus lacking anti-Gal epitopes).

GENERAL DESCRIPTION OF THE INVENTION

The present invention relates to the field of microbial vaccines in general and influenza virus vaccines in particular. In particular the present invention provides compositions and methods for induction of a potent immune response by targeting a microbial antigen of interest to antigen presenting cells (APC) of a recipient. As described herein, this targeting is achieved by exploiting the natural anti-Gal antibody, which is the most abundant natural antibody in humans constituting ~1% of immunoglobulins. This antibody interacts specifically with the carbohydrate epitope called the α-gal epitope with the structure Galα1-3Galβ1-4GlcNAc-R, or Galα1-3Galβ1-3GlcNAc-R. In one embodiment, the invention provides methods of propagating vaccine flu virus in bird, human, ape or Old World monkey cells (e.g., Vero cells) that are engineered to synthesize a-gal epitopes by stable transfection of the cells with the α1,3galactosyltransferase (α1,3GT) gene and selection for cells that have high activity of this gene. The present invention also provides methods of administering flu virus expressing α-gal epitopes (flu$_{αgal}$) to a subject having anti-Gal antibodies, which results in effective anti-Gal targeting of the flu virus to APC. In further embodiments, the present invention provides immunogens comprising a fusion between an N-linked glycoprotein (e.g., influenza virus hemagglutinin) and a polypeptide antigen of interest (e.g., microbial peptide or protein), and enzymatic processing of the fusion protein to carry α-gal epitopes. In one embodiment, the immunogen comprises of a fusion protein between influenza virus hemagglutinin and the influenza virus peptide M2e, and enzymatic processing of this fusion protein to carry α-gal epitopes, in order to elicit humoral immune responses in subjects having anti-Gal antibodies. In one embodiment, the immunogen comprises of a fusion protein between influenza virus hemagglutinin and the influenza virus nucleoprotein (NP), and enzymatic processing of this fusion protein to carry α-gal epitopes, in order to elicit a cellular immune response in subjects having anti-Gal antibodies.

DETAILED DESCRIPTION OF THE INVENTION

As described herein, the present invention provides methods and compositions for increasing the immunogenicity of inactivated flu virus immunogens (also referred to as subunit flu vaccines) through the production of influenza virus expressing α-gal epitopes in a cell line (e.g., Vero cell line) engineered to express high levels of the glycosylation enzyme α1,3galactosyltransferase (α1,3GT). This ensures effective anti-Gal mediated targeting of influenza virus to antigen presenting cells (APC) of a vaccine recipient. The present invention also provides methods and compositions for using influenza virus hemagglutinin (HA) as a platform for targeting protein antigens of interest (e.g., M2e and NP) to APC. In exemplary embodiments, this is achieved by production of recombinant fusion proteins between HA and M2e (HA-M2e) and between HA and NP (HA-NP), and by synthesis of α-gal epitopes on the HA portion of these fusion proteins. The α-gal epitopes on the HA portion of these recombinant proteins bind anti-Gal, which effectively targets these immunogens to APC resulting in the induction of potent immune responses to HA and M2e or HA and NP in subjects having endogenous anti-Gal antibodies.

I. Targeting Antigens to Antigen Presenting Cells (APC)

In general, a prerequisite for efficacy of a flu vaccine is the effective uptake of inactivated flu virus at the inoculation site by APC (e.g., dendritic cells and macrophages). In general, this prerequisite applies to influenza virus subunit vaccines comprising HA and NA, as well as other types of recombinant protein vaccines. APC internalizing the subunit vaccine transport it from the vaccination site to draining lymph nodes, where they present the immunogenic viral peptides on cell surface MHC class I and class II molecules for the activation of virus specific CD8+ and CD4+ T cells respectively (Zinkernagel et al., *Immunol Rev* 156:1, 1997). Activated CD4+ T cells are essential as helper T cells (Th cells) for providing help to virus specific B cells for the production of anti-viral antibodies. The Th cells further provide help to CD8+ T cells to become CTL that specifically destroy flu virus infected cells. Since currently used flu vaccines lack markers that identify them for uptake by APC at the vaccination site, the uptake of these subunit vaccines by APC is suboptimal as it is primarily mediated by random pynocytosis.

One of the most effective methods for active in situ targeting of vaccines to APC is by formation of immune complexes with the corresponding IgG molecules (e.g., opsonization). This targeting occurs because APC (including dendritic cells, Langerhans cells of the skin and macrophages) all express FcγR for the Fc portion of the antigen bound IgG antibody (Unkeless, *J Clin Inves* 83:355, 1989; and Clynes et al., *Proc Natl Acad Sci USA* 95:652, 1998). This interaction between the Fc portion of the opsonizing antibodies and FcγR on APC is considered the most effective mechanism by which APC identify and to internalize antigens for induction of a robust immune response (Regnault et al., *J Exp Med* 189:371, 1999). Accordingly, administration of vaccinating antigens in the form of immune complexes was found to increase immunogenicity by 10-1000 fold, with tetanus toxoid (Manta et al., *J Exp Med* 173:37, 1991), hepatitis B antigen (Celis and Chang, *Science* 224.297, 1984), Eastern equine encephalomyelitis vines (Houston et al., *J Infect Dis* 135:600, 1977) and simian immunodeficiency virus (Villinger et al., *J Virol* 77:10, 2003). The present invention exploits the natural anti-Gal antibody for targeting of flu vaccines to APC of humans, apes, Old World primates and birds, thereby increasing their efficacy in eliciting both specific and cross-protective immune responses.

II. Anti-Gal Mediated Targeting of Antigens to APC

Anti-Gal is a unique natural antibody that is the most abundant antibody in humans constituting ~1% of serum IgG (20-100 µg/ml) (Galili et al., *J Exp Med* 160:1519, 1984). This antibody interacts specifically with the α-gal epitope (Galα1-3Galβ1-4GlcNAc-R or Galα1-3Galβ1-3GlcNAc-R) on glycolipids and glycoproteins (Galili, *Springer Semin Immunopathol* 15:155, 1993). Anti-Gal is produced throughout life as a result of antigenic stimulation by bacteria of the gastrointestinal flora (Galili et al., *Infect Immun* 56:1730, 1988). The α-gal epitope is absent in humans, but is synthesized by the glycosylation enzyme α1,3galactosyltransferase (α1,3GT) in very large amounts in cells of non-primate mammals, prosimians and in New World monkeys (Galili et al., *J Biol Chem*, 263:17755, 1988). The α1,3GT gene was inactivated in ancestral Old World primates. Thus, humans, apes, and Old World monkeys all lack α-gal epitopes, but produce the anti-Gal antibody in large amounts (Galili, supra, 1993). Anti-Gal binds avidly in vivo to α-gal epitopes introduced into humans, or Old World monkeys. This is particularly evident in xenotransplantation, where the in vivo binding of anti-Gal to α-gal epitopes on transplanted pig heart or kidney is the main cause for the rapid rejection of such grafts in humans and in Old World monkeys (Galili, *Immunol Today* 14:480, 1993; and Collins et al., *J Immunol* 154:5500, 1995). This in situ interaction of anti-Gal with α-gal epitopes can be exploited for targeting viral envelope glycoproteins to APC. In fact, anti-Gal is the only antibody in humans that can serve for the purpose of targeting antigens to APC, because it is the only natural antibody known to be produced ubiquitously in large amounts in all humans (Galili, supra, 1993). Thus, any particulate or soluble antigen that has α-gal epitopes will form immune complexes with anti-Gal and will be targeted for effective uptake by APC (Galili, *Immunol Cell Biol* 83:674, 2005).

The immunogenicity of recombinant viral proteins expressing α-gal epitopes is assessed in an experimental animal model, the α1,3GT knockout mouse (KO mouse). Previously, the immunogenicity of a recombinant gp120 protein of the human immunodeficiency virus envelope was observed to increase upon treatment of the recombinant protein with neuraminidase and α1,3GT in vitro to yield an envelope glycoprotein bearing α-gal epitopes (Abdel-Motal et al., *J Virol* 80: 6943, 2006). In particular, a greater than 100 fold higher humoral and cellular immune responses were induced by immunization with a gp120 immunogen bearing α-gal epitopes, in comparison with a gp120 immunogen lacking these epitopes (Abdel-Motal et al., supra, 2006). This increased immunogenicity is thought to be achieved through the in vivo formation of immune complexes between anti-Gal and gp120 bearing α-gal epitopes (gp120$_{\alpha gal}$) that are targeted to APC at the inoculation site. These APC transport the internalized envelope glycoprotein to the draining lymph nodes where they present the immunogenic peptides on both MHC class I and class II molecules for the effective activation of CD8+ and CD4+ T cells, respectively. As described in more detailed herein, the present invention provides immunogens comprising an inactivated flu virus, a recombinant HA-M2e fusion protein and/or a recombinant HA-NP to target flu antigens to APC through formation of immune complexes with the natural anti-Gal antibody.

III. Preparation of Vero$_{\alpha GT}$ Cells for Propagation of Flu$_{\alpha Gal}$ Virus The preparation of flu vaccine differs from most other vaccines in clinical use, in that there is a time constraint of only six months from identification of the seasonal HA and NA sequences to vaccine delivery. In the event of a future pandemic outbreak of avian flu virus in human populations, this urgency is even greater because of the lethal outcome of this infection. Thus, the amount of flu vaccine prepared in such a short time period is limited.

Immunogenicity of vaccines can be maximized by targeting them effectively to APC, in order to enable their transport to lymph nodes, for processing and presentation of peptide epitopes for activation of T cells. Protection afforded by flu vaccines can be greatly increased if they also include a component for induction of a broad cross-protective immune response against conserved viral antigens such as the M2e peptide of the flu M2 protein, and the flu nucleoprotein (NP). As described herein the present invention exploits the to existence of natural anti-Gal antibody in human, apes, Old World monkeys and birds, for targeting of the inactivated virus immunogen to APC. For anti-Gal mediated targeting the flu virus immunogen should express multiple α-gal epitopes (flu$_{\alpha gal}$). Injection of inactivated flu$_{\alpha gal}$ in adjuvant results in the in situ binding of natural anti-Gal antibody to the α-gal epitopes on the vaccine virus (e.g., opsonization) and targeting of the vaccine to APC as illustrated in FIG. 1. The Fc portion of the opsonizing anti-Gal antibody binds to Fcγ receptors (FcγR) on APC, thereby inducing effective uptake of the flu virus by APC and the subsequent transport of the internalized virus by the APC to the draining lymph nodes. The flu virus internalized by the APC is further processed for presentation of flu virus peptides for the activation of flu virus specific T cells, thus, inducing an anti-flu cellular immune response. Similarly anti-Gal mediated targeting can be achieved with HA-M2e and HA-NP upon processing of these fusion proteins to bear α-gal epitopes on the HA component. A process for achieving expression of α-gal epitopes on flu virus by in vitro incubation with recombinant α1,3GT and with UDP-Gal has been described in U.S. Pat. Nos. 5,879,675 and 6,361,775 to Galili et al., herein incorporated by reference in their entirety. These processes of the prior art complicate the preparation of currently used flu vaccines since they require additional steps, including incubation of the flu virus with recombinant α1,3GT and with UDP-Gal and subsequent removal of α1,3GT and of UDP-Gal from the final vaccine preparation.

Recently, much research has been directed toward the use of African green monkey kidney cells (e.g., Vero cell line available as ATCC No. CCL-81) for propagation of 6+2 re-assorted flu virus by reverse genetics, for use in vaccine preparations (Govorkova et al., *J Virol* 70: 5519, 1996). The interest in propagation of flu virus for vaccine purposes in Vero cells, rather than in the traditional embryonated chicken egg systems, is due in large part to the difficulties in obtaining sufficient numbers of embryonated chicken eggs and to the tendency of flu virus HA to mutate for adaptation of growth in eggs. Thus, the World Health Organization has recommended using the Vero cell line for future production of flu virus immunogens. The flu virus currently used for vaccine preparation lacks α-gal epitopes because it is produced in embryonated chicken eggs lacking this epitope, since birds lack the α1,3GT enzyme (Galili et al., *J Biol Chem* 263:17755, 1988). Vero cells, planned for future propagation of vaccinating flu virus, also lack α1,3GT, since like all Old World monkeys, African green monkeys also lack an active α1,3GT enzyme (Galili supra, 1988).

Previously it has been shown that when Eastern Equine Encephalitis virus (EEEV) is propagated in the mouse 3T3 fibroblast cell line then the α-gal epitope is synthesized within the host cell on the EEEV envelope glycoprotein. In contrast, propagation of EEEV in Vero cells results in the production of an EEEV envelope glycoprotein lacking α-gal epitopes (Repik et al., *J Gen Virol,* 75:1177, 1994). These differences are associated with the production of the α1,3GT enzyme within mouse 3T3 fibroblasts and the absence of the α1,3GT in Vero cells, since the host cell glycosylation machinery synthesizes carbohydrate chains on viral glycoproteins.

The present invention circumvents the problems associated with the production of a suboptimal flu virus immunogen in cells (e.g., Vero cells) by providing compositions and methods for production of flu$_{\alpha gal}$ without the need for in vitro incubation with α1,3GT and UDP-Gal. For example, this is achieved by propagation of the virus in transgenic Vero cells (or other suitable human, ape or Old World monkey cell line) engineered to express an active α1,3GT enzyme. In some preferred embodiments, cells (e.g., Vero cells) are converted into cells that effectively synthesize α-gal epitopes on glycoproteins by heterologous expression of a functional α1,3GT gene (e.g., of a New World monkey or a non-primate mammal).

The following description uses Vero cells as an example. However, other non-tumorigenic cells lacking microbial contaminants (e.g., reverse transcript negative) could also be employed. Briefly to generate transgenic Vero cells with high α1,3GT activity (referred to as Vero$_{\alpha GT}$ cells) for effective synthesis of α-gal epitopes on virus glycoproteins in the Golgi apparatus, the competition from sialyltransferase must be minimized. The final stages in synthesis of carbohydrate chains on glycoproteins and glycolipids take place within the Golgi apparatus, by enzymes called collectively glycosyltransferases. α1,3Galactosyltransferase (α1,3GT) and sialyltransferase are two glycosyltransferases that compete with each other within the Golgi apparatus. Specifically these enzymes compete for capping carbohydrate chains with terminal N-acetyllactosamine carbohydrate chains (Galβ1-4GlcNAc-R) (See, center carbohydrate chain in FIG. 2) by galactose (Gal), to generate α-gal epitopes (Galα1-3Galβ1-4GlcNAc-R) (See, right carbohydrate chain in FIG. 2), or capping by sialic acid (SA) to generate sialylated carbohydrate chains (SA2-6Galβ1-4GlcNAc-R) (See, left carbohydrate chain in FIG. 2), respectively (Smith et al., *J Biol Chem* 265: 6225, 1990). Vero$_{\alpha GT}$ cells may be produced in two steps:

1) isolation of Vero cells with low sialyltransferase activity in order to minimize capping of carbohydrate chains by SA thereby increasing their accessibility to α1,3GT within the Golgi apparatus; and 2) stable transfection of Vero cells with low sialyltransferase activity with at least one active α1,3GT gene and selection of clones with high α1,3GT activity to maximize capping of carbohydrate chains by of α1,3GT within the Golgi apparatus.

Vero cells with minimal sialyltransferase activity are selected by sorting of cells that bind a fluoresceinated lectin. This lectin (e.g., *Datum starmonium* lectin) binds specifically to N-acetyllactosamine carbohydrate chains (Galβ1-4GlcNAc-R). The sorting may be performed within a cell sorter after cells are incubated with the lectin at decreasing concentrations (of the lectin). The cells binding the lectin at its lowest concentration are those with the highest number of N-acetyllactosamines that are not capped by SA (e.g., cells with the least sialyltransferase activity). These cells are isolated, expanded by incubation in tissue culture medium and transfected (e.g., electroporation) with a α1,3GT expression vector containing an antibiotic resistance gene (e.g., neomycin resistance) for a selection purposes. The transfected cells are grown in presence of a selection agent substance (e.g., G418) to obtain stable transfectants (e.g., transgenic Vero cells containing the α1,3GT gene within their genome. The α1,3GT gene can be any gene encoding an enzyme that synthesizes α-gal epitopes (e.g., any non-primate mammalian species). Non-limiting examples of suitable α1,3GT genes include but are not limited to the mouse α1,3GT coding region (GENBANK Accession No. NM_010283) and the pig α1,3GT coding region (GENBANK Accession No. NM_213810). Cells expressing α-gal epitopes are cloned by immunostaining with decreasing concentrations of fluoresceinated *Bancleiraea similicifolia* lectin (BS lectin specific for α-gal epitopes) and sorting of cells binding the lectin at the lowest concentration. Other suitable methods for selecting cells expressing α-gal epitopes include the immunostaining of cells with decreasing concentrations of a fluoresceinated anti-Gal antibody and sorting of cells binding the antibody at the lowest concentration. In some embodiments, the transgenic Vero cells engineered to express a first heterologous α1,3GT gene are subjected to a second round of transfection with a second expression vector containing the α1,3GT gene and a second selection marker (e.g., hygromycin resistance) and the subsequent growth of the transfected cells in the presence of a second selection agent (e.g., hygromycin). The second selection agent and selection marker can be any selection agent and selection marker that is different from first selection agent and first selection marker employed in the first round of transfection and selection. This transfection and selection process can be repeated one or more times, with each selection increasing the number of copies of heterologous, functional α1,3GT gene in the transfected cells. In certain embodiments, the selected cells expressing α-gal epitopes (Vero$_{\alpha GT}$ cells) are grown as individual clones and the clones with the highest expression of α-gal epitopes are further expanded.

The Vero$_{\alpha GT}$ cells are suitable for propagation of flu$_{\alpha gal}$ virus, since the hemagglutinin molecules of flu virus propagated in these cells are subjected to high α1,3GT activity and low sialyltransferase activity in the Golgi apparatus of the transgenic Vero$_{\alpha GT}$ cells. In certain embodiments, the flu$_{\alpha gal}$ virus produced in Vero$_{\alpha GT}$ cells undergoes the same vaccine preparation steps as that currently used for flu virus production in non-transgenic Vero cells (Govorkova et al., *J Virol,* 70: 5519, 1996). In an exemplary embodiment, the flu virus used to inoculate the Vero$_{\alpha GT}$ cells is a 6+2 re-assortment containing hemagglutinin (HA) and neuraminidase (NA) genes from a vaccine target strain and the remaining genes from A/Puerto Rico/8/34-H1N1 (PR8). In some embodiments, the vaccine target strain is an influenza A virus such as A/New Caledonia/20/99 (H1N1), A/Wisconsin/67/2005 (H3N2) or A/Hiroshima/52/2005 (H3N2), or an influenza B virus such as B/Malaysia/2506/2004 or B/Ohio/1/2005. Other suitable vaccine target strains are listed in the influenza sequence database accessible through the Los Alamos National Laboratory flu web site (Macken et al., *"The value of a database in surveillance and vaccine selection,"* in Options For The Control Of Influenza IV, Osterhaus et al. (Eds.) Amsterdam: *Elsevier Science,* pp. 103-106, 2001). Evaluation of α-gal epitope expression on flu virus propagated in Vero$_{\alpha GT}$ cells can be accomplished using the methods of experimental example 1 and as shown in FIG. 3A and FIG. 3B.

Since birds lack α-gal epitopes (Galili et al., *J Biol Chem* 263:17755, 1988) and naturally produce anti-Gal (Cotter et al., *Poult Sci* 85:435, 2006: and McKenzie et al., *Transplan-* tation 67:864, 1999), efficient anti-Gal mediated targeting of flu$_{\alpha gal}$ virus produced in Vero$_{\alpha GT}$ cells to APC of avian vaccine recipients is also contemplated to occur. Thus, the flu$_{\alpha gal}$ virus produced using the methods of the present invention is contemplated to be suitable vaccine for delivery to birds (e.g., including but not limited to chickens, turkeys, ducks and geese). Immunization of bird flocks with H5N1 flu$_{\alpha gal}$ virus (vaccine target strain such as A/Bar headed goose/Qinghai/1A/2005 or A/Whooping swan/Mongolia/244/2005) is contemplated to reduce circulation of avian influenza viruses in bird populations, which in turn is contemplated to reduce the spread of avian influenza viruses to humans.

IV. Hemagglutinin Expressing α-Gal Epitopes (HA$_{\alpha gal}$) as a Vaccine Platform As described herein the present invention also provides compositions and methods for production of fusion proteins comprising an HA component bearing α-gal epitopes (HA$_{\alpha gal}$) and a non-HA component (e.g., microbial protein or polypeptide antigen of interest) to increase opsonization of the non-HA component thereby increasing the immunogenicity of the non-HA component. In some preferred embodiments, the fusion protein comprises an HA component bearing α-gal epitopes (HA$_{\alpha gal}$) as a platform for anti-Gal mediated targeting to APC of one or both of the M2e peptide of the conserved flu virus matrix protein 2 (M2) peptide and the conserved flu virus nucleoprotein (NP). The HA$_{\alpha gal}$-M2e and HA$_{\alpha gal}$-NP fusion proteins are contemplated to be suitable for achieving a broad cross protective immune response against various influenza virus strains. In an exemplary embodiment, HA of avian influenza virus H5N1 is employed (influenza A virus A/Vietnam/CL2009/2005, GENBANK Accession No. DQ497729.1). Other suitable HA sequences are listed in the influenza sequence database accessible through the Los Alamos National Laboratory flu web site (Macken et al., "The value of a database in surveillance and vaccine selection," in Options For The Control Of Influenza IV, Osterhaus et al., (Eds.) Amsterdam: Elsevier Science, pp. 103-106, 2001).

The high mutation rate in HA reduces its suitability for use as vaccine for induction of broad protection against multiple flu virus strains. In contrast, the viral proteins M2 and NP are highly conserved as they undergo very low rates of mutation (Flynn et al., Proc Natl Acad Sci USA 96:8597, 1999; and Webster, Vaccine 18:1686, 2000). The M2 protein is abundant in the cell membrane of flu virus infected cells, but comprises <2% of proteins on the virus envelope (Mozdzanowska et al., Vaccine 21: 2616, 2003). Anti-M2e antibodies can target the outer region of M2 (23 amino acid ectodomain called M2e) expressed on the surface of flu virus-infected cells. These antibodies can mediate destruction of virus-infected cells through antibody-dependent cell-mediated cytotoxicity (ADCC). Similarly, It) effective induction of cytotoxic T lymphocytes (CTL) reactive with NP peptides presented on MHC class I molecules of flu virus-infected cells can mediate the killing of flu virus-infected cells. Effective anti-M2e antibody responses and anti-NP CTL responses are contemplated to contribute significantly to prevention of viral spread in the infected individual by these two mechanisms of antibody-mediated, or cell-mediated destruction of flu virus infected cells.

Previously, immunogenicity of recombinant M2e and NP was found to be very low (Mozdzanowska et al., Vaccine 21: 2616, 2003; and Zhang et al., Mol Immunol 43: 2195, 2006). This low immunogenicity is associated with suboptimal uptake of M2e and NP molecules by APC at the inoculation site. As described herein the present invention provides methods and compositions for induction of potent antibody responses against flu virus-infected cells expressing the M2e peptide and/or CTL responses against flu virus-infected cells presenting NP peptides in the context of MHC class I molecules. In some embodiments this is accomplished by generating recombinant fusion proteins between HA and M2e and between HA and NP, synthesis of α-gal epitopes on the multiple carbohydrate chains of the HA component, and the use of the HA$_{\alpha gal}$ component of the fusion protein as a platform for anti-Gal mediated targeting of M2e and/or NP to APC. In immunogens containing a HA$_{\alpha gal}$ component, endogenous anti-Gal antibodies of a recipient bind to α-gal epitopes on the HA component to target the M2e and/or NP components of the fusion proteins to APC.

Figure 8:
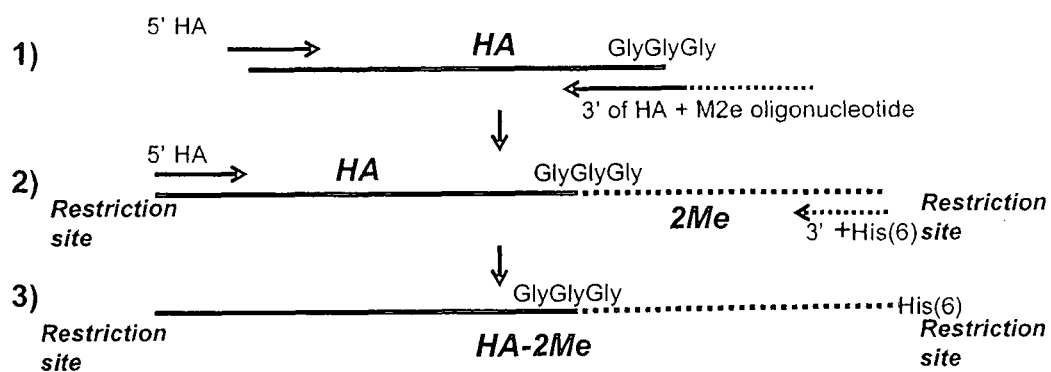

A process for achieving expression of α-gal epitopes on flu virus by in vitro incubation with recombinant α1,3GT and with UDP-Gal has been described in U.S. Pat. Nos. 5,879,675 and 6,361,775 to Galili et al., herein incorporated by reference in their entirety. However, the prior art patents did not disclose the use of HA$_{\alpha gal}$ as platform for targeting other microbial antigens to APC. In exemplary embodiments, HA is fused to M2e or NP to generate recombinant fusion proteins HA-M2e or HA-NP, as shown in FIG. 8 and FIG. 9. The HA-M2e and HA-NP fusion proteins are subsequently incubated with neuraminidase from Vibrio cholera and recombinant α1,3GT and with UDP-Gal to produce fusion proteins bearing α-gal epitopes on the amino-terminal HA component. Examples of HA-M2e and HA-NP production are included herein as Examples 6 and 7 respectively. The α-gal epitopes of the HA component are bound by anti-Gal of the recipient for targeting of the fusion proteins to APC, thereby increasing the immunogenicity of M2e and NP for eliciting a broad cross-protective immune response against infectious flu virus (See, to illustration in FIG. 1).

Figure 2:
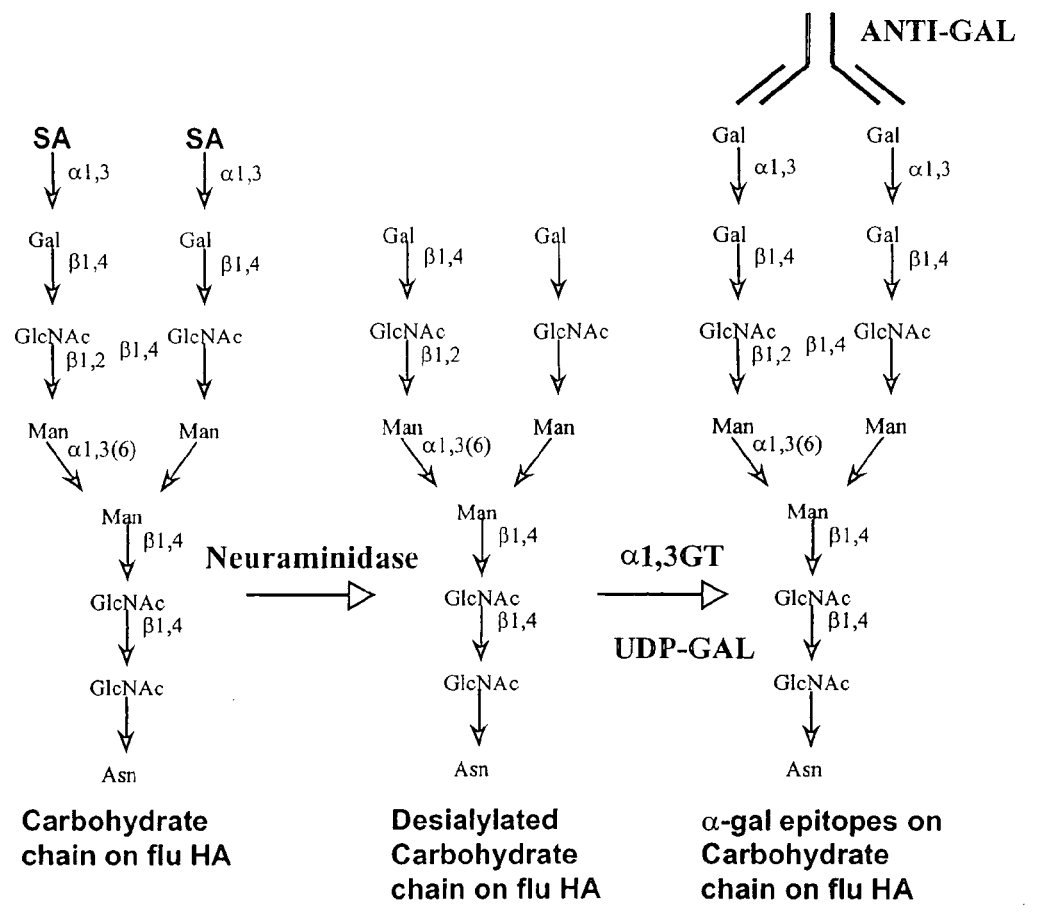

HA of flu virus has at least 6 asparagine (N)-linked carbohydrate chains, which when produced in CHO cells have the structure identical to the left-most carbohydrate chain in FIG. 2. As disclosed in U.S. Pat. Nos. 5,879,675 and 6,361,775 to Galili et al., the carbohydrate chains of flu HA can be engineered to express α-gal epitopes according to the reaction in FIG. 2 by removal of sialic acid (SA) on the carbohydrate chain by neuraminidase (left chain in FIG. 2 converted into the middle chain), and by α-gal epitope synthesis on that carbohydrate chain by recombinant α1,3GT and UDP-Gal (middle chain in FIG. 2 converted to the right chain). As described herein, the present invention provides compositions and methods for fusion of HA with M2e to generate a HA-M2e fusion gene, or for fusion of HA with NP to generate a HA-NP fusion gene. Expression vectors comprising the fusion genes in operable combination with a promoter are used to produce HA-M2e or HA-NP in mammalian cells (e.g., wild type CHO cells). Synthesis of α-gal epitopes on the carbohydrate chains of HA-M2e or NA-NP is achieved by treatment of the fusion proteins with a combination of neuraminidase, α1,3GT and UDP-Gal to generate HA$_{\alpha gal}$-M2e, or NA$_{\alpha gal}$-NP in which the HA portion carries multiple α-gal epitopes. Immunization of subjects (e.g., humans) having endogenous anti-Gal with HA$_{\alpha gal}$-M2e or HA$_{\alpha gal}$-NP results in the formation of immune complexes at the vaccination site and effective targeting of these fusion proteins to APC. Thus the immunogenicity of M2e and NP is contemplated to be increased by expression as a HA fusion proteins, even though the M2e and NP portions of the fusion proteins lack α-gal epitopes. The production of the HA-M2e and HA-NP expression vectors is not limited to the disclosure of Examples 6 and 7 and FIG. 8 and FIG. 9, since other standard molecular biology techniques can be used for this purpose. Production of the recombinant fusion proteins in mammalian cells such as CHO cells, or in transgenic mammals (e.g., production in mammary gland cells and secretion in milk) is performed according to standard methods known to those skilled in the art. The synthesis of cc-gal epitopes on the N-linked carbohydrate chains of the HA components of the HA-M2e and HA-NP fusion proteins is performed as shown in FIG. 2. The three types of vaccines flu$_{\alpha gal}$, HA$_{\alpha gal}$-M2e or HA$_{\alpha gal}$-NP, may be used individually, or in combinations of two or all three, for eliciting an anti-flu virus immune response that is contemplated to be protective (e.g., reduction of morbidity and mortality associated with flu virus invention).

Since birds lack α-gal epitopes (Galili et al., *J Biol Chem* 263:17755, 1988) and naturally produce anti-Gal (Cotter et al., *Poult Sci* 85:435, 2006; and McKenzie et al., *Transplantation* 67:864, 1999), efficient anti-Gal mediated targeting of HA$_{\alpha gal}$-M2e or HA$_{\alpha gal}$-NP to APC of avian vaccine recipients is also contemplated to occur. Thus, the HA$_{\alpha gal}$-M2e or HA$_{\alpha gal}$-NP fusion proteins produced using the methods of the present invention are contemplated to be suitable vaccine for delivery to birds (e.g., including but not limited to chickens, turkeys, ducks and geese). Immunization of bird flocks with H5-based HA$_{\alpha gal}$-M2e or HA$_{\alpha gal}$-NP fusion proteins is contemplated to reduce circulation of avian influenza viruses in bird populations, which in turn is contemplated to reduce the spread of avian influenza viruses to humans.

In further embodiments, synthesis of α-gal epitopes on the carbohydrate chains of HA-M2e or HA-NP is achieved by expression in host cells lacking the ability to add sialic acid caps to glycoproteins but having the ability to synthesize α-gal epitopes. Briefly, expression vectors comprising the fusion genes in operable combination with a promoter are transfected into host cells of a non-primate mammal having a defect in the cellular machinery required for sialic acid capping of carbohydrates to produce HA$_{\alpha gal}$-M2e, or NA$_{\alpha gal}$-NP without having to treat the recombinant fusion proteins in vitro with a combination of neuraminidase, α1,3GT and UDP-Gal. In some embodiments, the cells defective in the ability to add sialic acid caps are LEC29. Lec32 cells obtained from a mutagenized population of CHO cells following selection with wheat germ agglutinin as previously described (Potvin et al., *J Biol Chem*, 270: 30415-30421, 1995). In alternative embodiments, the cells defective in the ability to add sialic acid caps are other mutant cells of the prior art (Potvin et al., supra, 1995).

In still further embodiments, synthesis of α-gal epitopes on the carbohydrate chains of HA-M2e or HA-NP is achieved by expression in transgenic host cells having the ability to remove sialic acid caps from nascent glycoproteins, as well as the ability to synthesize α-gal epitopes. Briefly expression vectors comprising the fusion genes in operable combination with a promoter are transfected into transgenic host cells of a non-primate mammal comprising an expression vector comprising a flu neuraminidase gene in operable combination with a promoter to produce HA$_{\alpha gal}$-M2e, or NA$_{\alpha gal}$-NP, without having to treat the recombinant fusion proteins in vitro with a combination of neuraminidase, α1,3GT and UDP-Gal. In some embodiments, the transgenic host cells are MDCK cells (ATCC No. CCL-34) or NIH/3T3 cells (ATCC No. CCL-1658) engineered to express a flu neuraminidase gene. In further embodiments, the transgenic host cells lack endogenous α1,3GT activity, such as Vero cells (ATCC No. CCL-81) or CHO cells, and are therefore transfected with one or more expression vectors comprising a flu neuraminidase gene and a functional α1,3GT gene. Production of HA$_{\alpha gal}$-M2e, or NA$_{\alpha gal}$-NP in such transgenic cells is achieved without having to treat the recombinant fusion proteins in vitro with a combination of neuraminidase, α1,3GT and UDP-Gal. In some particularly preferred embodiments, a single expression vector drives expression of the heterologous neuraminidase and α1,3GT genes from a single promoter by separation of the genes with an internal ribosomal entry site (IRES).

The previous description uses HA as an exemplary glycoprotein carrier. However, other proteins comprising one or more N-linked glycosylation sites may be employed as the amino-terminal component of an immunogenic fusion protein. Other suitable glycoprotein carriers include but are not limited to HIV gp120 (Abdel-Motal et al., *J Virol*, 80:6943-6951), human hepatitis B surface antigen, and human alpha-1 acid glycoprotein (AGP), and human laminin. In still further embodiments, an artificial polypeptide (GGGNGSGGGNGTGGGNGSGGGNGTGGG set forth as SEQ ID NO:12) comprising multiple (e.g., 4) N-linked glycosylation sites is utilized as a glycoprotein carrier. In preferred embodiments, the glycoprotein carrier comprises at least two and more preferably from two to ten (e.g., two, three, four, five, six, seven, eight, nine or ten) N-linked glycosylation sites defined as N-X-S/T, wherein N is asparagine, X is any amino acid except proline, S is serine and T is threonine.

The artificial polypeptide can be recombinantly produced by expression behind a leader sequence and in front of microbial polypeptide of interest. Alternatively, the artificial polypeptide can be produced synthetically, chemically conjugated to a microbial polypeptide of interest, and treated with neuraminidase, α1,3GT and UDP-Gal in vitro to produce an immunogen bearing α-gal epitopes. Similarly, the artificial polypeptide-microbial polypeptide fusion can be produced synthetically and treated with neuraminidase, α1,3GT and UDP-Gal in vitro to produce an immunogen bearing α-gal epitopes. Likewise, a microbial polypeptide such as M2e (SEQ ID NO:10) can be produced synthetically, chemically conjugated to a purified glycoprotein such as AGP (Tanemura et al., *Transplantation*, 73:1859-1868, 2002), and treated with neuraminidase, α1,3GT and UDP-Gal in vitro to produce an immunogen bearing α-gal epitopes. In still further embodiments, other types of N-linked carriers are employed. For instance, α-gal epitopes can be synthesized on backbones such as gas914 and polyethylene glycol (Zhong et al., *Transplantation*, 75:10-19, 2003; and Diamond et al., *Transplantation*, 73:1780-1787, 2002), which subsequently can be chemically conjugated to a microbial polypeptide of interest.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: kDa (kilodalton); rec. (recombinant); N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); nil (milliliters); µl (microliters); cm (centimeters); mm (millimeters); µm (micrometers); nm (nanometers); C (degrees Centigrade); ELISA (enzyme linked immunosorbent assay); mAb (monoclonal antibody);

APC (antigen presenting cell); CTL (cytotoxic T lymphocyte); DC (dendritic cells); flu (influenza); HA (hemagglutinin); hemagglutination units (HAU); NA (neuraminidase); NP (nucleoprotein); PR8 (A/Puerto Rico/8/34-H1N1); Th (helper T); and IFNγ (interferon-γ).

EXAMPLE 1

In Vitro Synthesis of α-Gal Epitopes to Produce PR8$_{αgal}$

This example describes the synthesis of α-gal epitopes in the experimental flu virus strain A/Puerto Rico/8/34-H1N1 (PR8). This example is also applicable to the synthesis of α-gal epitopes on the fusion proteins HA-M2e and HA-NP to generate fusion proteins HA$_{αgal}$-M2e and/or HA$_{αgal}$-NP, which are contemplated to induce broad cross-protective immune responses against flu virus infection when used in vaccine formulations.

The PR8 virus produced in embryonated eggs was incubated with 30 μg/ml of recombinant (rec.) α1,3GT and 0.1 mM UDP-Gal (uridine diphosphate-galactose) as a sugar donor. The enzyme transfers the galactose from UDP-Gal and links it in a Galα1-3 linkage to the N-acetyllactosamines (Galβ1-4GlcNAc-R) of the multiple HA carbohydrate chains to generate α-gal epitopes, in a reaction that is identical to that naturally occurring within the Golgi apparatus of non-primate mammalian cells (middle chain to right chain in FIG. 2).

The de-novo synthesized α-gal epitopes on PR8 could be detected by Western blot (FIG. 3A) with mouse serum anti-Gal and with the anti-Gal mAb called M86 (Galili et al., *Transplantation* 65: 1129, 1998), and by ELISA with monoclonal anti-Gal (FIG. 3B). Separation of PR8 proteins by SDS-PAGE under reducing conditions demonstrates the distinct band of HA1 (~60 kDa) and a much weaker band of HA2 (~27 kDa), as well as other viral proteins in the range of 20-40 kDa. Blotting of the proteins followed by staining with mouse serum anti-Gal, or with the anti-Gal mAb M86 demonstrated the distinct staining of the HA1 band in the PR8$_{αgal}$ but not of the band of this size in the unprocessed PR8 virus sample (FIG. 3A). The binding of these antibodies is highly specific and was not observed with other proteins of the PR8$_{αgal}$ virus or with any of the proteins of PR8 virus. These findings indicate that the synthesis of α-gal epitopes by rec. α1,3GT occurs primarily on the carbohydrate chains of HA1.

Figure 3:
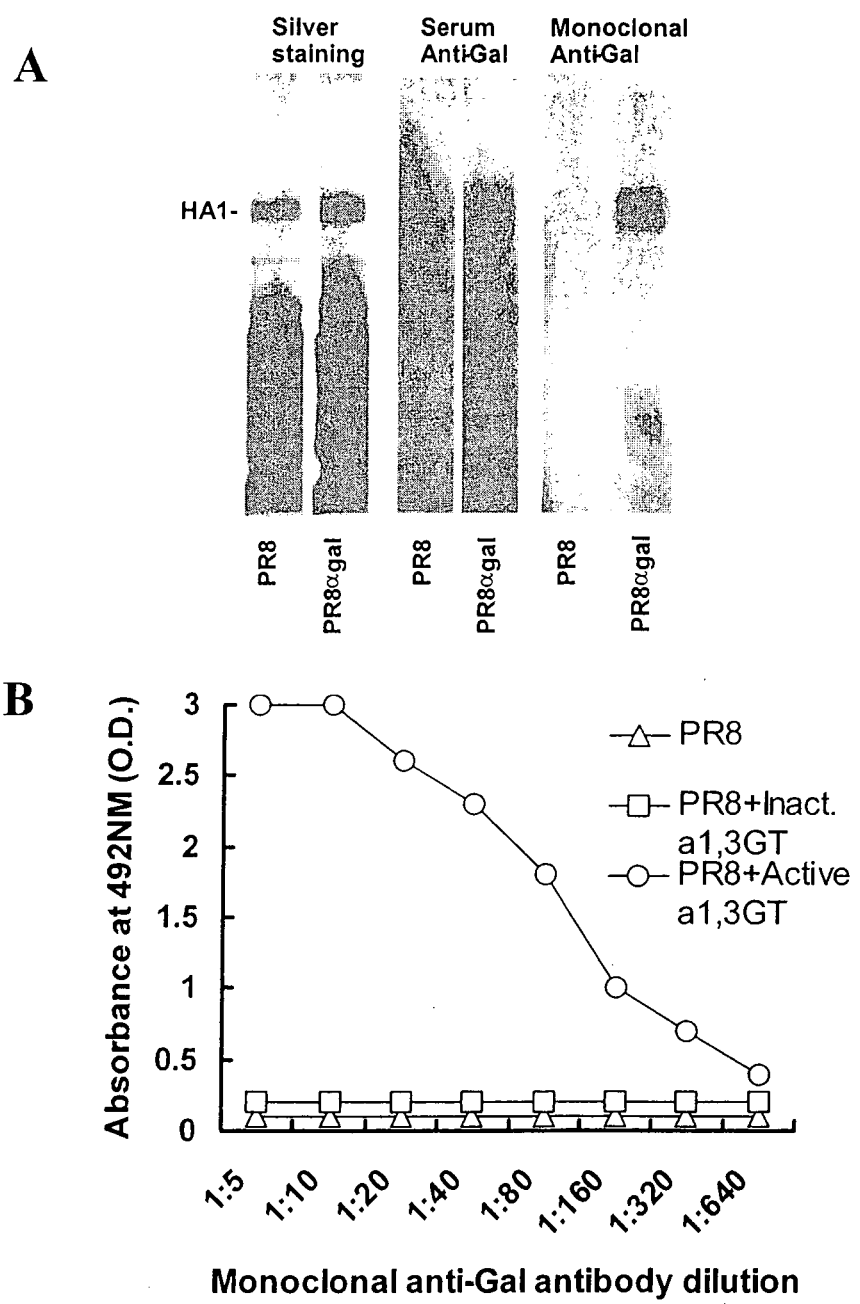

Additionally, expression of α-gal epitopes on PR8$_{αgal}$ was demonstrated on the intact virus as determined by ELISA with the anti-Gal mAb M86 and intact viruses as solid phase antigens. As shown in FIG. 3B, M86 bound to PR8$_{αgal}$ as a solid phase antigen in ELISA wells, but not to unprocessed PR8 virus or to PR8 virus incubated with heat-inactivated (e.g., boiled) rec. α1,3GT and UDP-Gal. The findings in FIG. 3 indicate that α-gal epitopes are readily synthesized on the multiple carbohydrate chains of HA of the intact virus. In a similar fashion, synthesis of α-gal epitopes can be achieved on glycoproteins of other microbial pathogens, as well as fusion proteins comprising a glycoprotein component (e.g., HA-M2e or HA-NP to generate HA$_{αgal}$-M2e or HA$_{αgal}$-NP).

EXAMPLE 2

ELISPOT Analysis of T Cell Responses in Mice Immunized with PR8$_{αgal}$ or PR8

The T cell response to flu virus antigens following vaccination with PR8$_{αgal}$ virus in comparison to vaccination with PR8 virus was studied in the experimental animal model, the α1,3GT knockout mice (KO mice) in which the exon containing the catalytic domain of the enzyme was disrupted by insertion of a neomycin resistance gene (Thall et al., *J Biol Chem* 270:21437, 1995). The KO mice effectively produce anti-Gal after 3-4 immunizations with pig kidney membrane (PKM) homogenates. The characteristics of this anti-Gal are very similar to those of human anti-Gal (Abdel-Motel et al., *J Virol,* 80: 6943, 2006). KO mice producing anti-Gal were immunized twice in bi-weekly intervals with 1 μg inactivated PR8$_{αgal}$, virus or with inactivated PR8 virus. The inactivation was achieved by incubation of the viruses for 45 min at 64° C., and confirmed by demonstration of a complete loss of chicken red blood cell (ChRBC) hemagglutinating activity. The inactivated virus was injected subcutaneously in Ribi (trehalose dicorynomycolate) adjuvant.

Figure 4:
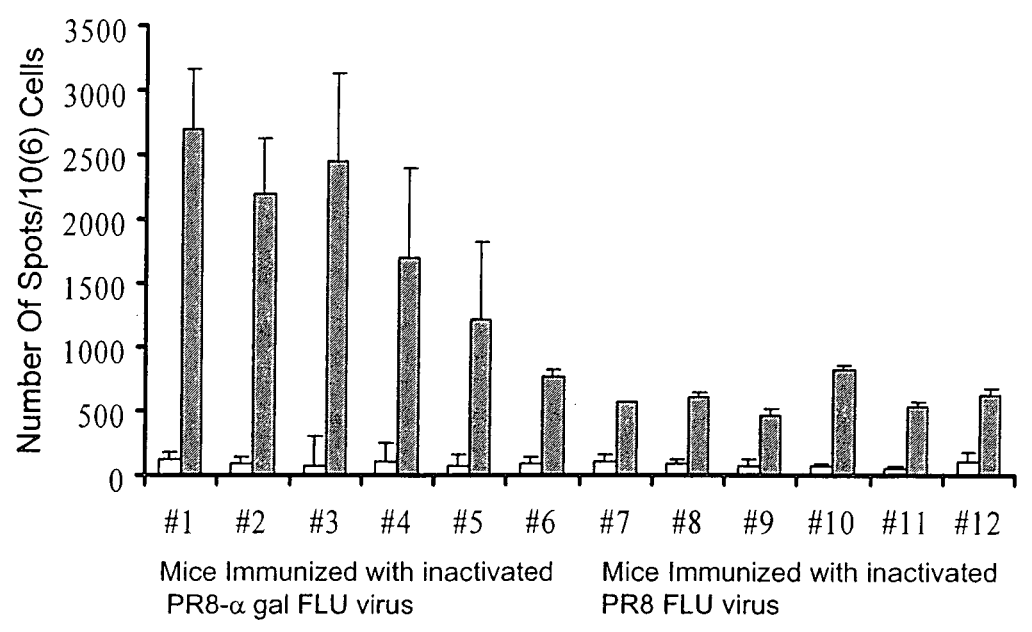

The mice were studied for anti-PR8 immune response 4 weeks after the second immunization. PR8-specific T cells were detected in the spleens of the immunized mice by ELISPOT assays, which measured secretion of interferon-γ (IFNγ) following stimulation in vitro by PR8 antigens presented on dendritic cells (DC). Briefly, KO mouse DC were incubated for 24 h with inactivated PR8, then co-incubated for an additional 24 h with spleen lymphocytes from the mice immunized with PR8$_{αgal}$ or PR8 virus. PR8-specific T cells stimulated by DC presenting immunogenic PR8 peptides, secrete IFNγ, which binds to the anti-IFNγ antibody coating the bottom of the ELISPOT well at the secretion site. After washing the wells, the site of the secreting T cell is detected as a spot by alkaline phosphatase coupled anti-IFNγ antibody. The number of T cells that secrete IFNγ in the absence of stimulatory PR8 did not exceed 50 per $10^6$ lymphocytes in any of the mice tested (open columns in FIG. 4). In mice immunized twice with the inactivated unprocessed PR8 virus (mice #7-12), the number of activated virus specific T cells ranged between 400 and 700 per $10^6$ lymphocytes, with an average±standard deviation of 510±103 spots/$10^6$ cells. The number of PR8 specific T cells in 4 of the 6 mice immunized with PR8$_{αgal}$ (mice #1-4) was several fold higher and ranged between 1650 and 2510 per $10^6$ lymphocytes. In the remaining two mice the number of these T cells was 750 and 1200 per $10^6$ lymphocytes. The average±standard deviation of the ELISPOT values in the mice immunized with PR8$_{αgal}$ was 1800±760. These studies indicate that flu$_{αgal}$ virus is much more immunogenic than flu virus lacking α-gal epitopes. This is because anti-Gal binding to the α-gal epitopes on the vaccinating virus enhances viral opsonization (e.g., targeting the vaccinating virus for effective uptake by APC). Nonetheless, knowledge of the mechanism(s) involved is not required in order to make and use the present invention.

EXAMPLE 3

Increased PR8 Specific CD8+ and CD4+ T Cell Responses Following PR8$_{αgal}$ Immunization as Measured by Intracellular Cytokine Staining (ICS)

Figure 5:
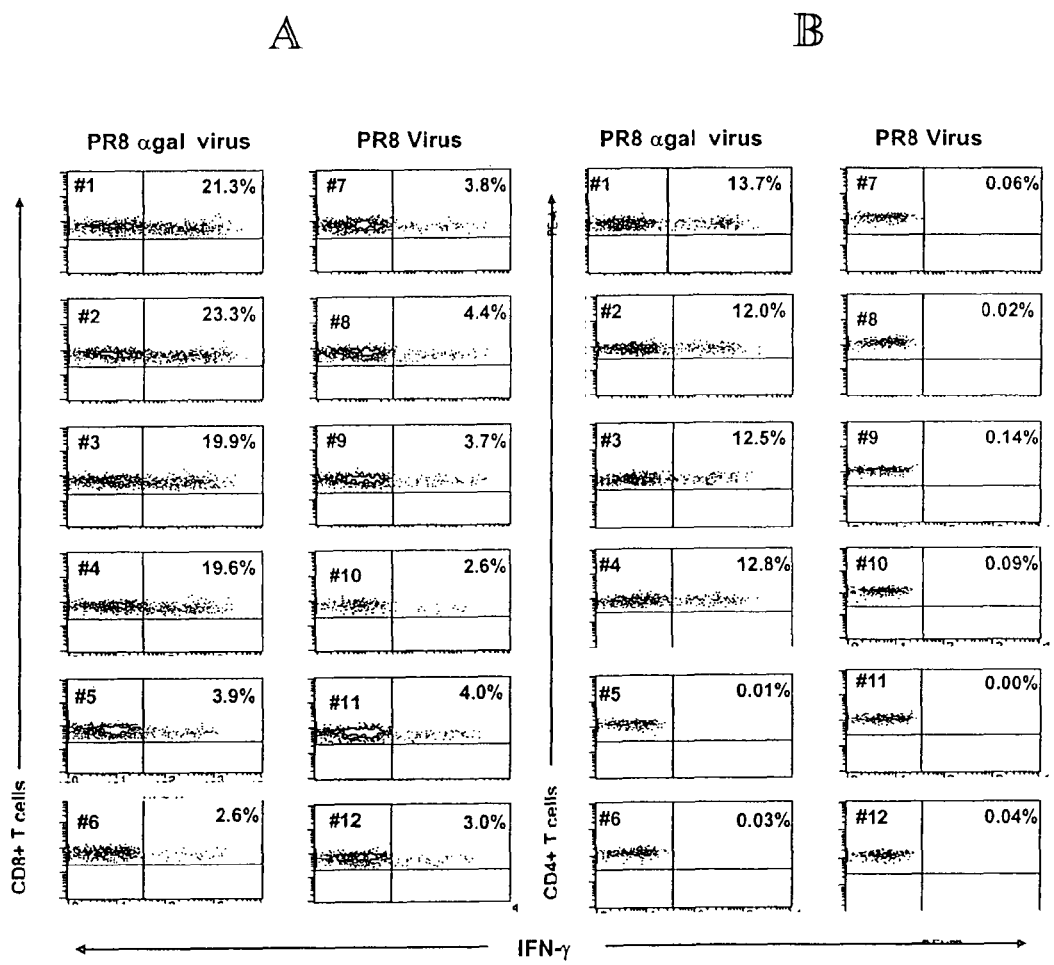
Figure 6:
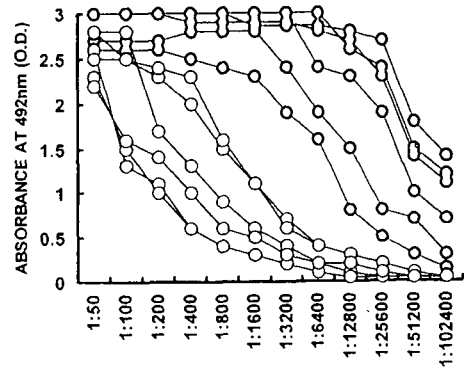
Figure 6:
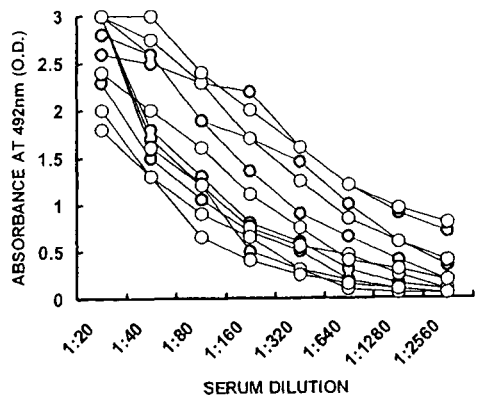
Figure 6:
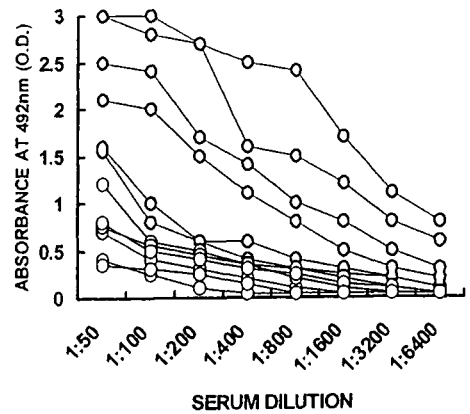

In order to determine whether the virus specific T cells in mice immunized with PR8 or PR8$_{αgal}$ include both CD8+ T cells (CTL precursors) and CD4+ T cells (Th1 cells) intracellular cytokine staining (ICS) methods were employed. Briefly, the ICS methods utilized involved the detection of IFNγ production in activated T cells that were also stained with CD8 or CD4 specific antibodies. The spleen lymphocytes from immunized mice were co-incubated for 24 h with DC that process PR8 proteins (due to pulsing with PR8) as in the ELISPOT assays above. However, cytokine secretion was prevented by treatment with brefeldin. Subsequently, the cells were washed, permeabilized and stained for intracellular IFNγ using a labeled anti-IFNγ antibody and an anti-CD8 or an anti-CD4 antibody. As shown in FIG. 5A, only 2.6-4.4% of CD8+ T cells from PR8 immunized mice were primed by PR8 pulsed DC and thus were only marginally activated. In contrast, in 4 mice immunized with $PR8_{\alpha gal}$ (#1-#4), as many as 19.5-23.3% of CD8+ T cells were activated by PR8 pulsed DC. The two mice (#5 and #6) that displayed low ELISPOT values as described in the previous example, also displayed low ICS levels in CD8+ T cells.

The differential response of T cells to the PR8 peptides presented by DC was also observed among the CD4+ T cells. Four of the mice immunized with $PR8_{\alpha gal}$ displayed 12-13.7% activation of CD4+ T cells, whereas no significant activation of such cells was observed among CD4+ T cells from PR8 immunized mice (FIG. 5B). CD4+ cells activated to produce IFNγ represent the PR8 specific Th1 population. The two $PR8_{\alpha gal}$ immunized mice (#5 and #6) with low levels of CD8+ activation, also had low levels of CD4+ activation, indicating that there was no measurably increased anti-virus cellular immune response in these mice as determined by ICS. As in the ELISPOT studies above, the ICS studies indicate that $flu_{\alpha gal}$ virus is much more immunogenic than flu virus lacking α-gal epitopes.

EXAMPLE 4

Increased Production of Anti-PR8 Antibodies Following $PR8_{\alpha Gal}$ Immunization This example describes the humoral immune response elicited in mice by administration of the α-gal epitope-bearing influenza virus strain, $PR8_{\alpha Gal}$.

1. Enzyme Linked Immunosorbent Assay (ELISA).

Anti-Gal titers in mice immunized with pig kidney membrane and the level of production of anti-PR8 antibodies were determined by ELISA as previously described (Abdel-Motal et al., J Virol, 80:6943-6951, 2006). Briefly, ELISA wells were coated with α-Gal BSA (10 μg/ml) or PR8 virus (1 μg/ml) overnight at 4° C. The plates were washed once with PBS and blocked with 1% BSA in PBS. Serum samples at various dilutions (50-μl aliquots) were plated in the wells for 2 h at room temperature. After the plates were washed, HRP-coupled goat anti-mouse IgG or goat anti-mouse IgA was added for 1 h. Color reactions were developed with ortho-phenylene diamine, and absorbance was measured at 492 nm. In assays using the monoclonal anti-Gal antibody M86 (Galili et al., Transplantation, 65:1129-1132, 1998), HRP-anti-mouse IgM was used as a secondary antibody. For antibody analysis within the sera, the first dilution was 1:10, whereas for analysis of the supernatants of lung homogenates, the first dilution was 1:1.

The sera from KO mice immunized with PR8 or $PR8_{\alpha gal}$ were assayed for antibodies to the unprocessed PR8 virus used as solid phase antigen in an ELISA. As shown in FIG. 6A, the anti-PR8 IgG antibody activity in the 6 mice immunized with inactivated $PR8_{\alpha gal}$ virus was much higher than in PR8 immunized mice. The four mice immunized with $PR8_{\alpha gal}$ that showed very high anti-PR8 antibody activity (mice #1-#4) displayed an average of 50% maximum binding (e.g., 1.5 OD) at the serum dilution of 1:102,400. Even in mice #5 and #6, which displayed low levels of CD4+ and CD8+ activation, displayed 50% maximum anti-PR8 IgG activity at serum dilution of 1:12,800 and 1:6,400, respectively. In contrast, in mice immunized with inactivated PR8 virus (e.g., virus lacking α-gal epitopes), the 50% maximum binding was observed in serum dilution of 1:400 (e.g., >200 fold lower than in $PR8_{\alpha gal}$ immunized mice #1-#4).

To determine whether the differences in antibody responses observed in the PR8 or $PR8_{\alpha gal}$ immunized KO mice are associated with anti-Gal, C57BL/6 wild type (WT) mice were also immunized with PR8 or $PR8_{\alpha gal}$. The WT mice express α-gal epitopes on their cells and thus, do not produce anti-Gal despite repeated (e.g., 4) immunizations with pig kidney membranes (PKM). As shown in FIG. 6B, no significant differences in anti-PR8 antibody responses were observed between PR8 and $PR8_{\alpha gal}$ immunized WT mice. Thus, in the absence of anti-Gal, the expression of α-gal epitopes on the immunizing virus has no measurable effect on the immunogenicity of the virus.

The differential humoral immune response in KO mice immunized with $PR8_{\alpha gal}$ versus those immunized with PR8 is also evident by analysis of anti-PR8 IgA antibodies in an ELISA employing PR8 virus as a solid phase antigen. The significance of this immunoglobulin class is primarily in mucosal immunity that prevents viral infection of respiratory tract cells. As shown in FIG. 6C, in $PR8_{\alpha gal}$ immunized mice #1-#4 anti-PR8 to IgA activity was 50-100 fold higher than observed in the PR8 immunized mice #7-#12. The antibody activity in serum dilution of 1:50 in mice #7-#12 was similar to the activity in serum dilution of 1:3,200 to 1:6,400 of mice #1-#4.

The anti-PR8 antibody studies indicate that $flu_{\alpha gal}$ virus is much more immunogenic than flu virus lacking α-gal epitopes. Thus, immunization with $flu_{\alpha gal}$ virus induces more potent humoral as well as cellular immune responses in recipients possessing anti-Gal antibodies.

II. Hemagglutinin Inhibition (HI) Assay.

One of the distinct antibody activities that protects against infection by the influenza virus is that of antibodies binding to the HA of the infectious virus, indicated by the prevention of subsequent binding of this envelope glycoprotein to target cells for infection. The ability of anti-HA antibodies to inhibit viral agglutination of ChRBC was measured as described previously (Galili et al., Vaccine, 14:321-328, 1996). Briefly, 5 HAU/ml of PR8 virus was plated in 96-well V-bottom plates (Corning). Sera were diluted in PBS containing 0.08% sodium azide. Aliquots of sera at serial twofold dilutions (beginning with a serum dilution of 1:10) were added to the virus and incubated overnight at 4° C. Subsequently, 50 μl of 1% ChRBC suspension was added and incubated for 30 min at room temperature. HA inhibition (HI) titers were determined as the highest serum dilution at which the hemagglutination of ChRBC was inhibited.

The level of HI activity in $PR8_{\alpha gal}$-immunized KO mice was many times higher than that in PR8-immunized mice. The average HI titer in the former group was 1:135, whereas in the latter group it was 1:15, (nine-fold lower). Two mice (#5 and #6) among the $PR8_{\alpha gal}$-immunized mice displayed a much lower level of HI activity, in agreement with other immune response parameters. On the other hand, the average level of HI activity in the highly responsive mice in that group (#1 to #4) is 1:180, which is 12-fold higher than in the control group immunized with unmodified PR8.

EXAMPLE 5

Induction of a Protective Immune Response Against Challenge with PR8

Mice were immunized twice with 1 μg of inactivated PR8 or $PR8_{\alpha gal}$ virus in the Ribi adjuvant at a bi-weekly interval.

Four weeks after the second immunization the mice were studied for resistance to challenge with 2000 plaque-forming units (PFU) of live PR8 virus in 50 μl administered via the nostrils (e.g., intranasally). Each group included 26 mice. The mice were monitored for mortality every day for 30 days post challenge.

Figure 7:
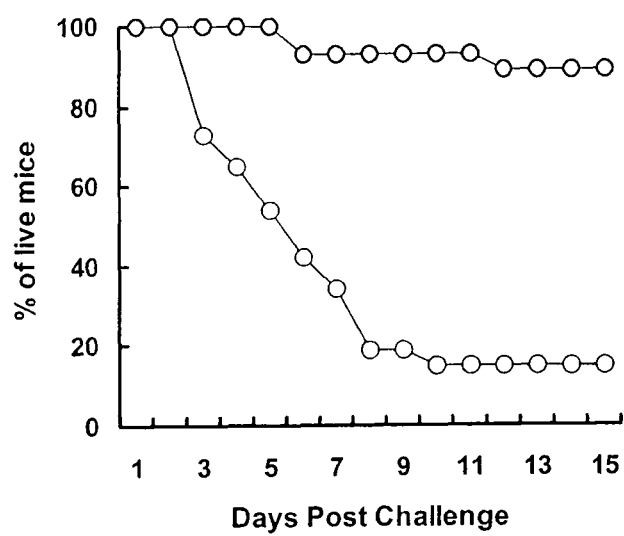

Most mice (85%) immunized with inactivated PR8 virus were not resistant to the intranasal viral challenge and died within 10 days post challenge with the live PR8 virus. As shown in FIG. 7, only 15% of the mice immunized with inactivated PR8 survived 10 days post challenge. In contrast, mice immunized with inactivated PR8$_{\alpha gal}$ virus were much more resistant to the live virus challenge. Only 11% of the mice immunized with inactivated PR8$_{\alpha gal}$ succumbed to the live virus and died, whereas 89% of the mice survived the challenge (FIG. 7). These experiments demonstrate that the heightened immune response induced by immunization of KO mice with inactivated PR8$_{\alpha gal}$ virus is physiologically significant in that it is associated with decreased mortality after a lethal flu virus challenge.

In separate studies, mice immunized with PR8$_{\alpha gal}$ or PR8 were euthanized 3 days post-challenge, and their lungs were harvested and homogenized in PBS to a total volume of 1 ml. The virus titers in supernatants of the homogenate were determined by measuring the tissue culture infectious dose (TCID) in MDCK cell monolayers (e.g., determine highest dilution resulting in cytopathic effect) and the hemagglutination of ChRBC. Incubation of the virus at serial 10-fold dilutions with MDCK cells for 96 h indicated that two of the PR8$_{\alpha gal}$-immunized mice had TCIDs of 100 and the remaining three mice had TCIDs of 10 (e.g., a dilution of 1:10 was the highest dilution resulting in a cytopathic effect on MDCK cells). In contrast, four of the five PR8-immunized mice had TCIDs of 1,000 and only one had a TCID of 100. The average TCID among the PR8$_{\alpha gal}$-immunized mice was approximately 18-fold lower than that in PR8-immunized mice. This difference in the presence of live PR8 in the lungs of the PR8-challenged mice was confirmed by analysis of the hemagglutination titers with ChRBC. Incubation of lung homogenate supernatants from PR8$_{\alpha gal}$-immunized mice with ChRBC resulted in hemagglutination titers (reciprocal of end point dilution displaying agglutination) of 50 for four mice and 100 for one mouse. In contrast, the titer for three of the PR8-immunized mice was 1,000, and for the remaining two mice it was 10,000.

One of the factors preventing virus infection and subsequent virus production in the lung cells of the PR8$_{\alpha gal}$-immunized mice is likely the anti-PR8 IgA antibody activity in the lungs. The activity of these antibodies was determined with an ELISA with serial twofold dilutions of the supernatants from lung homogenates. The lung homogenates from PR8-immunized mice contained no detectable anti-PR8 IgA antibodies, whereas those from all five PR8$_{\alpha gal}$-immunized mice had distinct anti-PR8 IgA activity. The lack of detectable anti-PR8 IgA antibodies in the lungs of PR8-immunized mice corresponds to the low level of such antibodies in the sera of PR8-immunized mice and suggests that the level of these antibodies in the lungs is beneath the detection level for ELISA.

EXAMPLE 6

Production of HA$_{\alpha gal}$-M2e Fusion Protein

This example provides an exemplary method for producing a HA-M2e recombinant fusion protein for subsequent preparation of a HA$_{\alpha gal}$-M2e immunogen. The steps illustrated in FIG. 8 are a blue print for the generation of a HA-M2e fusion protein. Step 1 involves the amplification by PCR of the HA sequence (excluding the transmembrane and cytoplasmic domain) of a flu virus of interest, using as the 5' primer an oligonucleotide sequence containing a first restriction enzyme site and nucleotides of the 5' region of HA (e.g., 5'HA primer), and as the 3' primer an oligonucleotide sequence containing nucleotides encoding the 23 amino acid oligopeptide of M2e, nucleotides encoding a tri-glycine linker and 15 nucleotides of the 3' region of HA but not including the stop codon (e.g., 3'HA primer), from an HA nucleic acid template. The M2e amino acid sequence of PR8 (SLLTEVETPIRNEWGSRSNDSSD set forth as SEQ ID NO:10 encoded by 5'-agtcttctaa ccgaggtcga aacgcttatc agaaacgaat gggggtgcag atgcaacggt tcaagtgat-3' set forth as SEQ ID NO:11) is based on a published M2e sequence (Mozdzanowska et al., Vaccine, 21:2616-2626, 2003). Step 2 involves the amplification by PCR of a HA-M2e fusion gene, using as the 5' primer the 5'HA primer described in step 1, and as the 3' primer an oligonucleotide sequence containing a second restriction enzyme site, a stop codon, nucleotides encoding a polyhistidine (His$_6$) tag, and nucleotides corresponding to the 3' region of M2e (3'M2e primer), from the purified PCR product of step 1 (template). The 5'HA primer contains a different restriction site from that of the 3'M2e primer to permit directional cloning. Step 3 involves cloning of the fused HA-M2e gene into a suitable vector for expression of the HA-M2e fusion protein in mammalian cells.

The HA-M2e fusion gene is inserted into an expression vector (e.g., Invitrogen pVAX1) containing a promoter active in mammalian cells (e.g., cytomegalovirus promoter) and a selectable marker (e.g., kanamycin resistance gene). Although the exemplary embodiment comprises the leader sequence of HA, other leader sequences may be used in place of this leader sequence (e.g., secretion signal from the V-J2-C region of mouse 1 g kappa chain). The plasmid transfected into a suitable host cell (e.g., Chinese hamster ovary cells) by a suitable method (e.g., electroporation), and kanamycin-resistant clones found to secrete large amounts of the HA-M2e fusion protein are selected (e.g., as determined by ELISA or western blot). After expansion of suitable clones, the fusion protein secreted from the cells into the culture medium is isolated by affinity chromatography (e.g., by binding to a nickel-sepharose column via the polyhistidine tag as previously described by Chen et al., Glycobiology 11:577, 2001). The generation of HA-M2e fusion proteins is not limited to the method described above and may be accomplished by other molecular biology methods known to those skilled in the art. Although the exemplary embodiment involves the use of culture cells for expression of the fusion protein, other types of systems may be employed in alternative embodiments (e.g., secretion into milk of transgenic animals engineered to express the fusion protein in cells of the mammary gland).

The purified fusion protein bound to nickel-Sepharose beads via the polyhistidine tag is subjected to synthesis of α-gal epitopes by incubation with neuraminidase, recombinant α1,3GT and UDP-Gal. Briefly the enzymatic reactions shown in FIG. 2 are performed simultaneously in an enzyme buffer containing 0.1 M MES (methyl ethyl morpholinosulfonate), pH 6.0, and 25 mM MnCl$_2$ as previously described for the synthesis of α-gal epitopes on influenza virus hemagglutinin (Henion et al., Vaccine, 15:1174-1182, 1997), on the bovine serum glycoprotein fetuin (Chen et al., supra, 2001), and on the human serum glycoprotein al, acid glycoprotein (Tanemura et al., Transplantation 73:1859-1868, 2002). The terminal sialic acid is removed by neuraminidase (1 mU/ml), and α-gal epitopes are synthesized on the HA-M2e by recombinant α1,3GT (30 µg/ml) and UDP-Gal (1 mM). The two enzymes are mixed in the same solution buffer and incubated with HA-NP (1 mg/ml) for 4 h at 37° C. At the end of the incubation period, the resulting HA$_{αgal}$-M2e is eluted from the beads with imidazole and subsequently prepared in an adjuvant for immunization purposes.

EXAMPLE 7

Production of a HA$_{αgal}$ NP Fusion Protein

This example provides an exemplary method for producing a HA-NP recombinant fusion protein for subsequent preparation of a HA$_{αgal}$-NP immunogen. The steps illustrated in FIG. 9 are a blue print for the generation of a HA-NP fusion protein. Step 1 involves the amplification by PCR of a HA gene (excluding the transmembrane and cytoplasmic domain) and an NP gene from virus nucleic acids. The HA gene is amplified using as the 5' primer an oligonucleotide sequence containing a first restriction enzyme site and nucleotides corresponding to the 5' region of HA (5'HA primer), and as the 3' primer an oligonucleotide sequence encoding a tri-glycine linker and nucleotides corresponding to the 3' region of HA (3'HA primer). The NP gene is amplified using as the 5' primer an oligonucleotide sequence containing nucleotides corresponding to a 3' region of HA, nucleotides encoding a tri-glycine linker and nucleotides corresponding to the 5' region of NP (5'NP primer), and as the 3' primer an oligonucleotide sequence containing a second restriction site (e.g., different from that of the 5'HA primer), a stop codon, nucleotides encoding a polyhistidine tag (six histidines) and nucleotides corresponding to the 3' region of NO (3'NP primer). Step 2 involves the amplification by PCR of a HA-NP fusion gene from the PCR products of the previous step (e.g., purified amplified HA and NP genes). In the initial cycles, the HA gene serves as 5' primer for the NP gene and the NP gene serves as 3' primer for the HA gene, to generate the fused HA-NP gene. In later cycles, the HA-NP fusion gene is further amplified using as the 5' and 3' primers, the 5' HA primer and the 3'NP primer of the previous step. Step 3 involves cloning of the fused HA-NP gene into a suitable vector for expression of the HA-NP fusion protein in mammalian cells.

The HA-NP fusion gene is inserted into an expression vector (e.g., Invitrogen pVAX1) containing a promoter active in mammalian cells (e.g., cytomegalovirus promoter) and a selectable marker (e.g., kanamycin resistance gene). Although the exemplary embodiment comprises the leader sequence of HA, other leader sequences may be used in place of this leader sequence (e.g., secretion signal from the V-J2-C region of mouse 1 g kappa chain). The plasmid transfected into a suitable host cell (e.g., Chinese hamster ovary cells) by a suitable method (e.g., electroporation), and kanamycin-resistant clones found to secrete large amounts of the HA-NP fusion protein are selected (e.g., as determined by ELISA or western blot). After expansion of suitable clones, the fusion protein secreted from the cells into the culture medium is isolated by affinity chromatography (e.g., by binding to a nickel-sepharose column via the polyhistidine tag as previously described by Chen et al., *Glycobiology* 11:577-586, 2001). The generation of HA-NP fusion proteins is not limited to the method described above and may be accomplished by other molecular biology methods known to those skilled in the art. Although the exemplary embodiment involves the use of culture cells for expression of the fusion protein, other types of systems may be employed in alternative embodiments (e.g., secretion into milk of transgenic animals engineered to express the fusion protein in cells of the mammary gland).

The purified fusion protein bound to nickel-Sepharose beads via the polyhistidine tag is subjected to synthesis of α-gal epitopes by incubation with neuraminidase, recombinant α1,3GT and UDP-Gal. Briefly the enzymatic reactions shown in FIG. 2 are performed simultaneously in an enzyme buffer containing 0.1 M MES (methyl ethyl morpholinosulfonate), pH 6.0, and 25 mM MnCl$_2$ as previously described for the synthesis of α-gal epitopes on influenza virus hemagglutinin (Henion et al., *Vaccine*. 15:1174-1182. 1997), on the bovine serum glycoprotein fetuin (Chen et al., supra, 2004 and on the human serum glycoprotein al, acid glycoprotein (Tanemura et al., *Transplantation* 73:1859-1868, 2002). The terminal sialic acid is removed by neuraminidase (1 mU/ml), and α-gal epitopes are synthesized on the HA-NP by recombinant α1,3GT (30 µg/ml) and UDP-Gal (1 mM). The two enzymes are mixed in the same solution buffer and incubated with HA-NP (1 mg/ml) for 4 h at 37° C. At the end of the incubation period, the resulting HA$_{αgal}$-NP is eluted from the beads with imidazole and subsequently prepared in an adjuvant for immunization purposes.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields are intended to be within the scope of the following claims.

I claim:

1. A method of producing influenza virus bearing multiple α-Gal epitopes, comprising: a) providing; i) an influenza virus; and ii) a transgenic host cell susceptible to infection by said influenza virus and comprising a recombinant nucleic acid sequence that is stably transfected in the genome of said transgenic host cell, wherein said recombinant nucleic acid sequence comprises a nucleotide sequence encoding α1,3galactosyltransferase (α1,3GT) in operable combination with a promoter, and wherein said transgenic host cell expresses a higher level of α1,3GT compared to a host cell lacking said recombinant nucleic acid sequence; and b) inoculating said transgenic host cell with said influenza virus to produce an inoculated host cell, wherein said inoculated host cell produces an influenza virus bearing multiple α-Gal epitopes.

2. The method of claim 1, wherein said influenza virus is an influenza A virus or an influenza B virus.

3. The method of claim 1, wherein said host cell is selected from the group consisting of a human cell, an ape cell, an Old World monkey cell and a bird cell.

4. The method of claim 3, wherein said Old World monkey cell is a Vero cell.

5. The method of claim 1, wherein said (α1,3GT) is an enzyme of a species selected from the group consisting of a mouse, a cow, a cat, a sheep, a rat, a pig and a New World monkey.

6. The method of claim 5, wherein said New World monkey is a common marmoset.

7. The method of claim 1, further comprising step c) inactivating said influenza virus bearing α-Gal epitopes to produce an inactivated influenza virus bearing α-Gal epitopes.

8. The method of claim 7, further comprising step d) administering said inactivated influenza virus bearing α-Gal epitopes to a subject having anti-Gal antibodies under conditions suitable for induction of an immune response by said subject.

9. The method of claim 8, wherein said immune response comprises production of antibodies reactive with said influenza virus and T lymphocytes reactive with cells infected by said influenza virus.

10. The method of claim 1, wherein said α-Gal epitopes comprise D-Gal-α1,3-D-Gal-β1,4-D-GlcNAc-R, wherein R is a glycolipid or a glycoprotein.

11. The method of claim 1, wherein said α-Gal epitopes comprise D-Gal-α1,3-D-Gal-β1,3-D-GlcNAc-R, wherein R is a glycolipid or a glycoprotein.

12. A method, comprising:
a) providing;
  i) an influenza virus; and
  ii) a transgenic host cell susceptible to infection by said influenza virus and comprising a recombinant nucleic acid sequence that is stably transfected in the genome of said transgenic host cell, wherein said recombinant nucleic acid sequence comprises a nucleotide sequence encoding an α1,3galactosyltransferase (α1,3GT) in operable combination with a promoter, and wherein said transgenic host cell expresses a higher level of α1,3GT and reduced sialyltransferase activity compared to a host cell lacking said recombinant nucleic acid sequence; and
b) inoculating said transgenic host cell with said influenza virus to produce an inoculated host cell, wherein said inoculated host cell produces an influenza virus bearing multiple α-Gal epitopes.

13. the method of claim 12, wherein said transgenic host cell is produced by
a) selecting a host cell that expresses reduced sialyltransferase activity to produce a selected cell, and b) transfecting said selected cell with a recombinant expression vector comprising a nucleic acid sequence encoding an α1,3galactosyltransferase (α1,3GT) in operable combination with a promoter.

* * * * *

UNITED STATES PATENT AND TRADEMARK OFFICE
CERTIFICATE OF CORRECTION

| | |
|---|---|
| PATENT NO. | : 9,662,383 B2 |
| APPLICATION NO. | : 12/450384 |
| DATED | : May 30, 2017 |
| INVENTOR(S) | : Uri Galili |

It is certified that error appears in the above-identified patent and that said Letters Patent is hereby corrected as shown below:

Please enter the following Statement of Government Support after the Description section and before the Field of Invention section:

Statement of Government Support

This invention was made with government support under Grant number AI058749 awarded by the National Institutes of Health. The Government has certain rights in the invention.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*